US012649933B2

(12) United States Patent
Zhang

(10) Patent No.: US 12,649,933 B2
(45) Date of Patent: Jun. 9, 2026

(54) CELLS HAVING GENE DUPLICATIONS AND USES THEREOF

(71) Applicant: Pfizer Inc., New York, NY (US)

(72) Inventor: Lin Zhang, Union, NJ (US)

(73) Assignee: Pfizer Inc., New York, NY (US)

( * ) Notice: Subject to any disclaimer, the term of this patent is extended or adjusted under 35 U.S.C. 154(b) by 581 days.

(21) Appl. No.: 18/007,178

(22) PCT Filed: Jul. 27, 2021

(86) PCT No.: PCT/IB2021/056803
§ 371 (c)(1),
(2) Date: Jan. 27, 2023

(87) PCT Pub. No.: WO2022/023972
PCT Pub. Date: Feb. 3, 2022

(65) Prior Publication Data
US 2023/0287455 A1 Sep. 14, 2023

Related U.S. Application Data

(60) Provisional application No. 62/706,075, filed on Jul. 30, 2020.

(51) Int. Cl.
*C12N 15/90* (2006.01)
(52) U.S. Cl.
CPC ................................... *C12N 15/90* (2013.01)
(58) Field of Classification Search
CPC ....... C12N 15/90; C12N 15/907; C12N 15/63
See application file for complete search history.

(56) References Cited

FOREIGN PATENT DOCUMENTS

| | | |
|---|---|---|
| JP | 2016-127817 A | 7/2016 |
| WO | 2007/123489 | 11/2007 |
| WO | 2022/023972 A1 | 2/2022 |

OTHER PUBLICATIONS

GenBank LMNB1_Human. 2019. GenBank. 1-12. (Year: 2019).*
Singh RK et al. Protein Engineering Approaches in the Post-Genomic Era. 2017. Current Protein and Peptide Science. 18, 1-11. (Year: 2017).*
Zanigni S et al. Brain magnetic resonance metabolic and microstructural changes in adult-onset autosomal dominant leukodystrophy. 2015. Brain Research Bulletin. 117, 14-31. (Year: 2015).*
Zhang M et al. Propagated Perturbations from a Peripheral Mutation Show Interactions Supporting WW Domain Thermostability. 2018. Structure. 26, 1474-1485. (Year: 2018).*
Mattanovich D et al: "Stress in recombinant protein producing yeasts", Journal of Biotechnology, Elsevier, Amsterdam NL, vol. 113, No. 1-3, Sep. 30, 2004 (Sep. 30, 2004), pp. 121-135.
Wang Z et al: "Enhancement of therapeutic monoclonal antibody production in CHO cells using 30Kc6 gene", Dec. 1, 2010 (Dec. 1, 2010), Process Biochemistry, Elsevier Ltd, GB, pp. 1852-1856.
Zhao X et al: "Overexpression of survivin and cyclin DI in CHO cells confers apoptosis resistance and enhances growth in serum-free suspension culture", Biotechnology Letters, Springer Netherlands, Dordrecht, vol. 33, No. 7, Mar. 5, 2011 (Mar. 5, 2011), pp. 1293-1300.
Dhara, V.G., et al., "Recombinant Antibody Production in CHO and NSO Cells: Differences and Similarities," BioDrugs, 2018, 32:571-584.
International Preliminary Report on Patentability issued in PCT/IB2021/056803; mailed on Feb. 9, 2023; 7 pp.
International Search Report issued in PCT/IB2021/056803; mailed on Oct. 27, 2021; 6 pp.
Trask, B.J. and Hamlin, J.L., "Early Dihydrofolate Reductase Gene Amplification Events in CHO Cells Usually Occur on the Same Chromosome Arm as the Original Locus," Genes & Development, 1989, 3:1913-1925.
Written Opinion issued in PCT/IB2021/056803; mailed on Oct. 27, 2021; 5 pp.

* cited by examiner

*Primary Examiner* — Paul J Holland

(57) ABSTRACT

Host cells having improved growth characteristics are provided. Also provided are methods of selecting, using, and making the cells.

17 Claims, 1 Drawing Sheet

Specification includes a Sequence Listing.

SEQUENCE LISTING

```
<160> NUMBER OF SEQ ID NOS: 10

<210> SEQ ID NO 1
<211> LENGTH: 785
<212> TYPE: PRT
<213> ORGANISM: Cricetulus griseus

<400> SEQUENCE: 1

Met Ala Gln Pro Ser Ser Pro Gly Gly Glu Gly Pro Gln Phe Gly Ala
1               5                   10                  15

Thr Gly Asp Ser Arg Asp Ala Leu Ser Leu Glu Glu Ile Leu Arg Leu
            20                  25                  30

Tyr Asn Gln Pro Ile Asn Glu Glu Gln Ala Trp Ala Val Cys Phe Gln
        35                  40                  45

Cys Cys Gly Ser Leu Arg Ala Thr Ala Ala Arg Arg Gln Pro His Arg
```

-continued

```
         50              55              60

Arg Val Arg Ser Ala Ala Gln Ile Arg Val Trp Arg Asp Gly Ala Val
65                  70                  75                  80

Thr Leu Ala Pro Ala Ala Gly Glu Glu Gly Glu Pro Pro Pro Ala Ser
                85                  90                  95

Gly Lys Leu Gly Tyr Ser His Cys Thr Glu Thr Glu Val Ile Glu Ser
               100                 105                 110

Leu Gly Ile Ile Ile Tyr Lys Ala Leu Asp Tyr Gly Leu Lys Glu Asn
               115                 120                 125

Glu Glu Arg Glu Leu Ser Pro Pro Leu Glu Gln Leu Ile Asp Gln Met
           130                 135                 140

Ala Asn Thr Val Glu Ala Asp Gly Asn Ser Asp Glu Gly Tyr Glu Ala
145                 150                 155                 160

Ala Asp Glu Gly Pro Glu Asp Glu Asp Gly Gly Lys Arg Asn Ile Ser
               165                 170                 175

Ala Ile Arg Ser Tyr Gln Asp Val Met Lys Ile Cys Ala Ala His Leu
               180                 185                 190

Pro Ala Glu Ser Glu Ala Pro Asn His Tyr Gln Ala Val Cys Arg Ala
           195                 200                 205

Leu Phe Ala Glu Thr Met Glu Leu His Thr Phe Leu Thr Lys Ile Lys
   210                 215                 220

Ser Ala Lys Glu Asn Leu Lys Lys Ile Gln Glu Met Glu Lys Thr Asp
225                 230                 235                 240

Glu Ser Ser Thr Asp Leu Glu Asp Leu Lys Asn Ala Asp Trp Ala Arg
               245                 250                 255

Phe Trp Val Gln Val Met Arg Asp Leu Arg Asn Gly Val Lys Leu Lys
               260                 265                 270

Lys Val Gln Gln Arg Gln Tyr Asn Pro Leu Pro Ile Glu Tyr Gln Leu
           275                 280                 285

Thr Pro Tyr Glu Met Leu Met Asp Asp Ile Arg Cys Arg Arg Tyr Thr
   290                 295                 300

Leu Arg Lys Val Met Val Asn Gly Asp Ile Pro Pro Arg Leu Arg Lys
305                 310                 315                 320

Ser Ala His Glu Ile Ile Leu Asp Phe Ile Arg Ser Arg Pro Pro Leu
               325                 330                 335

Asn Pro Ala Ser Ala Arg Lys Leu Lys Pro Thr Pro Pro Arg Pro Arg
               340                 345                 350

Ser Leu His Glu Arg Ile Leu Glu Glu Ile Lys Ala Glu Arg Lys Leu
           355                 360                 365

Arg Pro Val Ser Pro Glu Glu Ile Arg Arg Ser Lys Leu Asp Val Thr
   370                 375                 380

Thr Pro Asp Ser Ser Lys Asn Val Gly Glu Ser Ser Met Val Asn Gly
385                 390                 395                 400

Gly Leu Ala Ser Gln Thr Lys Glu Asn Gly Leu Gly Ala Ala Gln Pro
               405                 410                 415

Gly Pro Ala Gln Arg Lys Lys Leu Leu Lys Ala Pro Thr Leu Ala Glu
               420                 425                 430

Leu Asp Ser Ser Asp Ser Glu Glu Glu Thr Leu His Lys Ser Thr Ser
           435                 440                 445

Ser Ser Ser Ala Ser Pro Ser Leu Tyr Glu Asp Pro Val Leu Glu Ala
   450                 455                 460

Met Cys Thr Arg Lys Lys Pro Pro Lys Phe Leu Pro Ile Ser Ser Thr
465                 470                 475                 480
```

-continued

```
Pro Gln Pro Glu Arg Arg Gln Pro Pro Gln Arg Arg His Ser Ile Glu
                485                 490                 495

Lys Glu Thr Pro Thr Asn Val Arg Gln Phe Leu Pro Pro Ser Arg Gln
                500                 505                 510

Ser Ser Arg Ser Leu Val Pro Arg Ile Thr Ser Val Trp Pro Arg Thr
                515                 520                 525

Pro Phe Arg Pro Leu Phe Ser Thr Ile Gln Thr Ala Ser Leu Leu Ser
                530                 535                 540

Ser His Pro Phe Glu Ala Ala Met Phe Gly Val Ala Gly Ala Met Tyr
545                 550                 555                 560

Tyr Leu Phe Glu Arg Ala Phe Thr Ser Arg Trp Lys Pro Ser Lys Glu
                565                 570                 575

Glu Phe Cys Tyr Pro Val Glu Cys Leu Ala Leu Thr Val Glu Glu Val
                580                 585                 590

Met His Ile Arg Gln Val Leu Val Lys Ala Glu Leu Glu Lys Tyr Gln
                595                 600                 605

Gln Tyr Lys Asp Val Tyr Thr Ala Leu Lys Lys Gly Lys Leu Cys Phe
                610                 615                 620

Cys Cys Arg Thr Arg Arg Phe Ser Phe Phe Thr Trp Ser Tyr Thr Cys
625                 630                 635                 640

Gln Phe Cys Lys Arg Pro Val Cys Ser Gln Cys Cys Lys Lys Met Arg
                645                 650                 655

Leu Pro Ser Lys Pro Tyr Ser Thr Leu Pro Ile Phe Ser Leu Gly Pro
                660                 665                 670

Ser Ala Leu Gln Arg Gly Glu Ser Cys Pro Arg Pro Glu Lys Ser Ser
                675                 680                 685

Thr Ala His His Arg Pro Leu Arg Ser Ile Ala Arg Phe Ser Ser Lys
                690                 695                 700

Ser Lys Ser Val Asp Lys Ser Asp Glu Glu Leu Gln Phe Pro Lys Glu
705                 710                 715                 720

Phe Met Glu Asp Trp Ser Thr Met Glu Val Cys Val Asp Cys Lys Lys
                725                 730                 735

Phe Ile Ser Glu Ile Ile Ser Ser Ser Arg Arg Ser Leu Val Leu Ala
                740                 745                 750

Asn Lys Arg Ala Arg Leu Lys Arg Lys Thr Gln Ser Phe Tyr Met Ser
                755                 760                 765

Ser Ala Gly Pro Ser Glu Tyr Cys Pro Ser Glu Arg Thr Ile Asn Glu
    770                 775                 780

Ile
785

<210> SEQ ID NO 2
<211> LENGTH: 559
<212> TYPE: PRT
<213> ORGANISM: Cricetulus griseus

<400> SEQUENCE: 2

Met Ser Ser Glu Val Ile Arg Ala Thr Ala Gly Met Val Leu Ala Glu
1               5                   10                  15

Leu Tyr Val Ser Asp Arg Glu Gly Asn Asp Ala Thr Gly Asp Gly Thr
                20                  25                  30

Lys Glu Lys Pro Phe Lys Thr Gly Leu Lys Ala Leu Met Thr Val Gly
            35                  40                  45

Lys Glu Pro Phe Pro Thr Ile Tyr Val Asp Ser Gln Lys Glu Asn Glu
```

-continued

```
        50                55                60

Arg Trp Asp Val Ile Ser Lys Ser Gln Met Lys Asn Ile Lys Lys Met
65                  70                75                80

Trp His Arg Glu Gln Met Lys Asn Asp Ser Arg Glu Lys Lys Glu Ala
                85                90                95

Glu Asp Asn Leu Arg Arg Glu Lys Asn Leu Glu Glu Ala Lys Lys Ile
            100               105               110

Ile Ile Lys Asn Asp Pro Ser Leu Pro Glu Pro Ala Cys Val Lys Ile
            115               120               125

Cys Ala Leu Glu Gly Tyr Arg Gly Gln Arg Val Lys Val Phe Gly Trp
        130               135               140

Val His Arg Leu Leu Arg Glu Gly Lys Asn Leu Met Phe Leu Val Leu
145               150               155               160

Arg Asp Gly Thr Gly Tyr Leu Gln Cys Val Leu Ser Asp Asp Leu Cys
                165               170               175

Gln Cys Tyr Asn Gly Val Val Leu Ser Thr Glu Ser Ser Val Ala Val
            180               185               190

Tyr Gly Thr Leu Asn Leu Thr Pro Lys Gly Lys Gln Ala Pro Gly Gly
            195               200               205

His Glu Leu Ser Cys Asp Phe Trp Glu Leu Val Gly Leu Ala Pro Ala
        210               215               220

Gly Gly Ala Asp Asn Leu Ile Asn Glu Glu Ser Asp Val Asp Val Gln
225               230               235               240

Leu Asn Asn Arg His Met Met Ile Arg Gly Glu Asn Met Ser Lys Ile
                245               250               255

Leu Lys Ala Arg Ser Met Ile Thr Arg Cys Phe Arg Asp His Phe Phe
            260               265               270

Asp Arg Gly Tyr Cys Glu Val Thr Thr Pro Thr Leu Val Gln Thr Gln
            275               280               285

Val Glu Gly Gly Ala Thr Leu Phe Lys Leu Asp Tyr Phe Gly Glu Glu
        290               295               300

Ala Phe Leu Thr Gln Ser Ser Gln Leu Tyr Leu Glu Thr Cys Leu Pro
305               310               315               320

Ala Leu Gly Asp Val Phe Cys Ile Ala Gln Ser Tyr Arg Ala Glu Gln
            325               330               335

Ser Arg Thr Arg Arg His Leu Ala Glu Phe Thr His Val Glu Ala Glu
            340               345               350

Cys Pro Phe Leu Thr Phe Glu Asp Leu Leu Asn Arg Leu Glu Asp Leu
        355               360               365

Val Cys Asp Val Val Asp Arg Val Leu Lys Ser Pro Val Ala Ser Ile
    370               375               380

Val Tyr Asp Leu Asn Pro Asn Phe Lys Pro Lys Arg Pro Phe Arg
385               390               395               400

Arg Met Asn Tyr Ser Asp Ala Ile Glu Trp Leu Arg Glu His Asp Val
            405               410               415

Lys Lys Glu Asp Gly Thr Leu Tyr Glu Phe Gly Asp Asp Ile Pro Glu
            420               425               430

Ala Pro Glu Arg Leu Met Thr Asp Thr Ile Asn Glu Pro Ile Leu Leu
        435               440               445

Cys Arg Phe Pro Val Glu Ile Lys Ser Phe Tyr Met Gln Arg Cys Pro
    450               455               460

Glu Asp Pro Arg Leu Thr Glu Ser Val Asp Val Leu Met Pro Asn Val
465               470               475               480
```

```
Gly Glu Ile Val Gly Gly Ser Met Arg Ser Trp Asp Ser Glu Glu Ile
                485                 490                 495

Leu Glu Gly Tyr Lys Arg Glu Gly Ile Asp Pro Ala Pro Tyr Tyr Trp
                500                 505                 510

Tyr Thr Asp Gln Arg Lys Tyr Gly Thr Cys Pro His Gly Gly Tyr Gly
            515                 520                 525

Leu Gly Leu Glu Arg Phe Leu Ser Trp Ile Leu Asn Arg Tyr His Ile
        530                 535                 540

Arg Asp Val Cys Leu Tyr Pro Arg Phe Val Gln Arg Cys Arg Pro
545                 550                 555

<210> SEQ ID NO 3
<211> LENGTH: 151
<212> TYPE: PRT
<213> ORGANISM: Cricetulus griseus

<400> SEQUENCE: 3

Met Ala Pro Arg Lys Gly Lys Glu Lys Lys Glu Glu Gln Val Ile Ser
1               5                   10                  15

Leu Gly Pro Gln Val Ala Glu Gly Glu Asn Val Phe Gly Val Cys His
            20                  25                  30

Ile Phe Ala Ser Phe Asn Asp Thr Phe Val His Val Thr Asp Leu Ser
        35                  40                  45

Gly Lys Glu Thr Ile Cys Arg Val Thr Gly Gly Met Lys Val Lys Ala
    50                  55                  60

Asp Arg Asp Glu Ser Ser Pro Tyr Ala Ala Met Leu Ala Ala Gln Asp
65                  70                  75                  80

Val Ala Gln Arg Cys Lys Glu Leu Gly Ile Thr Ala Leu His Ile Lys
                85                  90                  95

Leu Arg Ala Thr Gly Gly Asn Arg Thr Lys Thr Pro Gly Pro Gly Ala
            100                 105                 110

Gln Ser Ala Leu Arg Ala Leu Ala Arg Ser Gly Met Lys Ile Gly Arg
        115                 120                 125

Ile Glu Asp Val Thr Pro Ile Pro Ser Asp Ser Thr Arg Arg Lys Gly
    130                 135                 140

Gly Arg Arg Gly Arg Arg Leu
145                 150

<210> SEQ ID NO 4
<211> LENGTH: 60
<212> TYPE: PRT
<213> ORGANISM: Cricetulus griseus

<400> SEQUENCE: 4

Met Asp Ala Ile Ser Gln Ser Pro Val Asp Val Leu Leu Pro Lys His
1               5                   10                  15

Ile Leu Asp Ile Trp Ala Ile Val Leu Ile Ile Leu Ala Thr Ile Val
            20                  25                  30

Ile Met Thr Ser Leu Phe Leu Cys Pro Ala Thr Ala Val Ile Ile Tyr
        35                  40                  45

Arg Met Arg Thr His Pro Val Leu Asn Gly Ala Val
    50                  55                  60

<210> SEQ ID NO 5
<211> LENGTH: 617
<212> TYPE: PRT
<213> ORGANISM: Cricetulus griseus
```

-continued

<400> SEQUENCE: 5

```
Met Asp Leu Lys Thr Ala Val Phe Asn Ala Ala Arg Asp Gly Lys Leu
1               5                   10                  15

Arg Leu Leu Thr Lys Leu Leu Ala Ser Lys Ser Lys Glu Glu Val Ser
            20                  25                  30

Ser Leu Ile Ser Glu Lys Thr Asn Gly Ala Thr Pro Leu Leu Met Ala
        35                  40                  45

Ala Arg Tyr Gly His Leu Asp Met Val Glu Phe Leu Leu Glu Gln Cys
    50                  55                  60

Ser Ala Ser Ile Glu Val Gly Gly Ser Val Asn Phe Asp Gly Glu Thr
65                  70                  75                  80

Ile Glu Gly Ala Pro Pro Leu Trp Ala Ala Ser Ala Ala Gly His Leu
                85                  90                  95

Lys Val Val Gln Ser Leu Leu Asn His Gly Ala Ser Val Asn Asn Thr
            100                 105                 110

Thr Leu Thr Asn Ser Thr Pro Leu Arg Ala Ala Cys Phe Asp Gly His
        115                 120                 125

Leu Glu Ile Val Lys Tyr Leu Val Glu His Lys Ala Asp Leu Glu Val
    130                 135                 140

Ser Asn Arg His Gly His Thr Cys Leu Met Ile Ser Cys Tyr Lys Gly
145                 150                 155                 160

His Lys Glu Ile Ala Gln Tyr Leu Leu Glu Lys Gly Ala Asp Val Asn
                165                 170                 175

Arg Lys Ser Val Lys Gly Asn Thr Ala Leu His Asp Cys Ala Glu Ser
            180                 185                 190

Gly Ser Leu Asp Ile Met Lys Met Leu Leu Met Tyr Cys Ala Lys Met
        195                 200                 205

Glu Lys Asp Gly Tyr Gly Met Thr Pro Leu Leu Ser Ala Ser Val Thr
    210                 215                 220

Gly His Thr Asn Ile Val Asp Phe Leu Thr His His Ala Gln Thr Ser
225                 230                 235                 240

Lys Thr Glu Arg Ile Asn Ala Leu Glu Leu Leu Gly Ala Thr Phe Val
                245                 250                 255

Asp Lys Lys Arg Asp Leu Leu Gly Ala Leu Lys Tyr Trp Lys Lys Ala
            260                 265                 270

Met Asn Met Arg Tyr Ser Asp Arg Thr Asn Ile Ile Ser Lys Pro Val
        275                 280                 285

Pro Gln Thr Leu Ile Met Ala Tyr Asp Tyr Ala Lys Glu Val Asn Ser
    290                 295                 300

Ala Glu Glu Leu Glu Gly Leu Ile Ala Asp Pro Asp Glu Met Arg Met
305                 310                 315                 320

Gln Ala Leu Leu Ile Arg Glu Arg Ile Leu Gly Pro Ser His Pro Asp
                325                 330                 335

Thr Ser Tyr Tyr Ile Arg Tyr Arg Gly Ala Val Tyr Ala Asp Ser Gly
        340                 345                 350

Asn Phe Lys Arg Cys Ile Asn Leu Trp Lys Tyr Ala Leu Asp Met Gln
        355                 360                 365

Gln Ser Asn Leu Asp Pro Leu Ser Pro Met Thr Ala Ser Ser Leu Leu
    370                 375                 380

Ser Phe Ala Glu Leu Phe Ser Phe Met Leu Gln Asp Arg Ala Lys Gly
385                 390                 395                 400

Leu Leu Gly Thr Thr Val Thr Phe Asp Asp Leu Met Gly Ile Leu Cys
```

-continued

```
                        405                 410                 415

Lys Ser Val Leu Glu Ile Glu Arg Ala Ile Lys Gln Thr Gln Cys Pro
                    420                 425                 430

Ala Asp Pro Leu Gln Leu Asn Lys Ala Leu Ser Ile Ile Leu His Leu
                    435                 440                 445

Ile Cys Leu Leu Glu Lys Val Pro Cys Thr Leu Glu Gln Asp His Phe
                    450                 455                 460

Lys Lys Gln Thr Ile Tyr Arg Phe Leu Lys Leu His Pro Arg Gly Lys
        465                 470                 475                 480

Asn Asn Phe Ser Pro Leu His Leu Ala Val Asp Lys Asn Thr Thr Cys
                    485                 490                 495

Val Gly Arg Tyr Pro Val Cys Lys Phe Pro Ser Leu Gln Val Thr Ala
                    500                 505                 510

Ile Leu Ile Glu Cys Gly Ala Asp Val Asn Val Arg Asp Ser Asp Asp
                    515                 520                 525

Asn Ser Pro Leu His Ile Ala Ala Leu Asn Asn His Pro Asp Ile Met
                    530                 535                 540

Asn Leu Leu Ile Lys Ser Gly Ala His Phe Asp Ala Thr Asn Leu His
        545                 550                 555                 560

Lys Gln Thr Ala Ser Asp Leu Leu Asp Glu Lys Glu Ile Ala Lys Asn
                    565                 570                 575

Leu Ile Gln Pro Ile Asn His Ile Thr Leu Gln Cys Leu Ala Ala Arg
                    580                 585                 590

Val Ile Val Asn His Arg Ile Tyr Tyr Lys Gly Asn Ile Pro Glu Lys
                    595                 600                 605

Leu Glu Thr Phe Val Ser Leu His Arg
                    610                 615

<210> SEQ ID NO 6
        <211> LENGTH: 212
        <212> TYPE: PRT
        <213> ORGANISM: Cricetulus griseus

<400> SEQUENCE: 6

Met Ile Pro Gly Pro Arg Leu Leu Leu Pro Ala Val Leu Cys Leu Gly
        1               5                   10                  15

Leu Gly Thr Leu Val Ser Ser Ser Gly Ser Ser Gly Val Arg Lys Arg
                    20                  25                  30

Gly Pro Ser Val Thr Ala Lys Val Phe Phe Asp Val Lys Ile Gly Asp
                    35                  40                  45

Lys Asp Val Gly Arg Ile Val Ile Gly Leu Phe Gly Lys Val Val Pro
                    50                  55                  60

Lys Thr Val Glu Asn Phe Val Ala Leu Ala Thr Gly Glu Lys Gly Tyr
        65                  70                  75                  80

Gly Tyr Lys Gly Ser Ile Phe His Arg Val Ile Lys Asp Phe Met Ile
                    85                  90                  95

Gln Gly Gly Asp Phe Thr Ala Arg Asp Gly Thr Gly Gly Met Ser Ile
                    100                 105                 110

Tyr Gly Glu Thr Phe Pro Asp Glu Asn Phe Lys Leu Lys His Tyr Gly
                    115                 120                 125

Ile Gly Trp Val Ser Met Ala Asn Ala Gly Pro Asp Thr Asn Gly Ser
                    130                 135                 140

Gln Phe Phe Ile Thr Leu Thr Lys Pro Ser Trp Leu Asp Gly Lys His
        145                 150                 155                 160
```

```
Val Val Phe Gly Lys Val Leu Asp Gly Met Thr Val Val His Ser Ile
            165                 170                 175

Glu Leu Gln Ala Thr Asp Asp His Asp Arg Pro Phe Thr Asp Cys Thr
            180                 185                 190

Ile Val Asn Ser Gly Lys Ile Asp Val Lys Thr Pro Phe Val Val Glu
            195                 200                 205

Val Pro Asp Trp
    210

<210> SEQ ID NO 7
<211> LENGTH: 455
<212> TYPE: PRT
<213> ORGANISM: Cricetulus griseus

<400> SEQUENCE: 7

Met Lys Leu Arg Glu Tyr Glu Ala Ala Leu Asn Ser Lys Asp Ala Ala
1               5                   10                  15

Leu Ala Thr Ala Leu Gly Asp Lys Lys Ser Leu Glu Gly Asp Leu Glu
            20                  25                  30

Asp Leu Lys Asp Gln Ile Ala Gln Leu Glu Ala Ser Leu Ser Ala Ala
            35                  40                  45

Lys Lys Gln Leu Ala Asp Glu Thr Leu Leu Lys Val Asp Leu Glu Asn
    50                  55                  60

Arg Cys Gln Ser Leu Thr Glu Asp Leu Glu Phe Arg Lys Asn Met Tyr
65                  70                  75                  80

Glu Glu Glu Ile Asn Glu Thr Arg Arg Lys His Glu Thr Arg Leu Val
            85                  90                  95

Glu Val Asp Ser Gly Arg Gln Ile Glu Tyr Glu Tyr Lys Leu Ala Gln
            100                 105                 110

Ala Leu His Glu Met Arg Glu Gln His Asp Ala Gln Val Arg Leu Tyr
            115                 120                 125

Lys Glu Glu Leu Glu Gln Thr Tyr His Ala Lys Leu Glu Asn Ala Arg
            130                 135                 140

Leu Ser Ser Glu Met Asn Thr Ser Thr Val Asn Ser Ala Arg Glu Glu
145                 150                 155                 160

Leu Met Glu Ser Arg Met Arg Ile Glu Ser Leu Ser Ser Gln Leu Ser
            165                 170                 175

Asn Leu Gln Lys Glu Ser Arg Ala Cys Leu Glu Lys Ile Gln Glu Leu
            180                 185                 190

Glu Asp Met Leu Ala Lys Glu Lys Asp Asn Ser Arg Arg Met Leu Ser
            195                 200                 205

Asp Lys Glu Arg Glu Met Ala Glu Ile Arg Asp Gln Met Gln Gln Gln
    210                 215                 220

Leu Asn Asp Tyr Glu Gln Leu Leu Asp Val Lys Leu Ala Leu Asp Met
225                 230                 235                 240

Glu Ile Ser Ala Tyr Arg Lys Leu Leu Glu Gly Glu Glu Glu Arg Leu
            245                 250                 255

Lys Leu Ser Pro Ser Pro Ser Ser Arg Val Thr Val Ser Arg Ala Ser
            260                 265                 270

Ser Ser Arg Ser Val Arg Thr Thr Arg Gly Lys Arg Lys Arg Val Asp
            275                 280                 285

Val Glu Glu Ser Glu Ala Ser Ser Ser Val Ser Ile Ser His Ser Ala
    290                 295                 300

Ser Ala Thr Gly Asn Val Cys Ile Glu Glu Ile Asp Val Asp Gly Lys
305                 310                 315                 320
```

-continued

```
Phe Ile Arg Leu Lys Asn Thr Ser Glu Gln Asp Gln Pro Met Gly Gly
                325                 330                 335

Trp Glu Met Ile Arg Lys Ile Gly Asp Thr Ser Val Ser Tyr Lys Tyr
                340                 345                 350

Thr Ser Arg Tyr Val Leu Lys Ala Gly Gln Thr Val Thr Ile Trp Ala
            355                 360                 365

Ala Asn Ala Gly Val Thr Ala Ser Pro Pro Thr Asp Leu Ile Trp Lys
        370                 375                 380

Asn Gln Asn Ser Trp Gly Thr Gly Glu Asp Val Lys Val Ile Leu Lys
385                 390                 395                 400

Asn Ser Gln Gly Glu Glu Val Ala Gln Arg Ser Thr Val Phe Lys Thr
                405                 410                 415

Thr Ile Pro Glu Glu Glu Glu Glu Glu Glu Glu Pro Ile Gly Val
                420                 425                 430

Val Ile Glu Glu Glu Arg Phe His Gln Gln Gly Ala Pro Arg Ala Ser
            435                 440                 445

Asn Arg Ser Cys Ala Ile Met
    450                 455

<210> SEQ ID NO 8
<211> LENGTH: 604
<212> TYPE: PRT
<213> ORGANISM: Cricetulus griseus

<400> SEQUENCE: 8

Met Ala Gly Gly Arg His Lys Pro Pro Ser Ala Ser Ser Trp Asn Arg
1               5                   10                  15

Val Arg Glu Lys Met Phe Ser Arg Val Arg Ala Ile Val Thr Pro Cys
                20                  25                  30

Thr Leu Thr Cys Arg His Leu His Leu Lys Glu Lys Gly Lys Pro Leu
            35                  40                  45

Met Leu Asn Pro Arg Thr Asn Lys Gly Met Ala Phe Thr Leu Gln Glu
        50                  55                  60

Arg Gln Met Leu Gly Leu Gln Gly Leu Leu Pro Pro Lys Ile Glu Thr
65                  70                  75                  80

Gln Asp Ile Gln Ala Leu Arg Phe His Arg Asn Leu Lys Lys Met Thr
                85                  90                  95

Ser Pro Leu Glu Lys Tyr Ile Tyr Ile Met Gly Ile Gln Glu Arg Asn
                100                 105                 110

Glu Lys Leu Phe Tyr Arg Ile Leu Gln Asp Asp Ile Glu Ser Leu Met
            115                 120                 125

Pro Ile Val Tyr Thr Pro Thr Val Gly Leu Ala Cys Ser Gln Tyr Gly
        130                 135                 140

His Ile Phe Arg Arg Pro Lys Gly Leu Phe Ile Ser Ile Ser Asp Arg
145                 150                 155                 160

Gly His Val Arg Ser Ile Val Asp Asn Trp Pro Glu Asn His Val Lys
                165                 170                 175

Ala Val Val Val Thr Asp Gly Glu Arg Ile Leu Gly Leu Gly Asp Leu
                180                 185                 190

Gly Val Tyr Gly Met Gly Ile Pro Val Gly Lys Leu Cys Leu Tyr Thr
            195                 200                 205

Ala Cys Ala Gly Ile Gln Pro Glu Lys Cys Leu Pro Val Cys Ile Asp
        210                 215                 220

Val Gly Thr Asp Asn Lys Ala Leu Leu Lys Asp Pro Phe Tyr Met Gly
```

-continued

```
225                 230                 235                 240

Leu Tyr Gln Lys Arg Asp Arg Ser Gln Leu Tyr Asp Asp Leu Ile Asp
            245                 250                 255

Glu Phe Met Lys Ala Ile Thr Asp Arg Tyr Gly Arg Asn Thr Leu Ile
            260                 265                 270

Gln Phe Glu Asp Phe Gly Asn His Asn Ala Phe Arg Phe Leu Arg Lys
            275                 280                 285

Tyr Arg Glu Lys Tyr Cys Thr Phe Asn Asp Asp Ile Gln Gly Thr Ala
    290                 295                 300

Ala Val Ala Leu Ser Gly Leu Leu Ala Thr Gln Lys Val Ile Asn Lys
305                 310                 315                 320

Pro Val Ser Glu His Lys Ile Leu Phe Leu Gly Ala Gly Glu Ala Ala
            325                 330                 335

Leu Gly Ile Ala Asn Leu Ile Val Met Ser Met Val Glu Ser Gly Leu
            340                 345                 350

Ser Glu Glu Glu Ala Arg Arg Lys Val Trp Met Phe Asp Lys Asn Gly
            355                 360                 365

Leu Leu Val Lys Gly Arg Ser Ala Ser Ile Asp Ser Asn Gln Glu Pro
    370                 375                 380

Phe Ala His Gly Ala Pro Glu Asn Val Pro Gly Thr Phe Glu Asp Ala
385                 390                 395                 400

Val Asn Lys Leu Lys Pro Ser Val Ile Ile Gly Val Ala Gly Ala Gly
            405                 410                 415

Arg Leu Phe Thr Pro Gly Val Ile Lys Ala Met Ala Ser Ile Asn Glu
            420                 425                 430

Arg Pro Ile Ile Phe Ala Leu Ser Asn Pro Thr Ala Gln Ala Glu Cys
            435                 440                 445

Thr Ala Glu Glu Ala Tyr Thr Leu Thr Glu Gly Arg Cys Leu Phe Ala
    450                 455                 460

Ser Gly Ser Pro Phe Glu Pro Val Lys Leu Gln Asp Gly Arg Val Phe
465                 470                 475                 480

Thr Pro Gly Gln Gly Asn Asn Ala Tyr Ile Phe Pro Gly Val Ala Leu
            485                 490                 495

Ala Val Ile Leu Cys Gln Thr Arg His Ile Ser Asp Ser Val Phe Leu
            500                 505                 510

Glu Ala Ala Lys Ala Leu Thr Ser Gln Leu Thr Asp Glu Glu Leu Ala
            515                 520                 525

Gln Gly Arg Leu Tyr Pro Ser Leu Ala Asn Ile Gln Glu Val Ser Val
    530                 535                 540

Asn Ile Ala Ile Lys Val Thr Glu Tyr Leu Tyr Ala Asn Lys Met Ala
545                 550                 555                 560

Phe Arg Tyr Pro Glu Pro Glu Asp Lys Ala Lys Tyr Val Lys Glu Arg
            565                 570                 575

Ile Trp Arg Ser Asp Tyr Val Ser Leu Leu Pro Asp Val Tyr Asp Trp
            580                 585                 590

Pro Glu Ser Ser Leu Lys Pro Pro Gln Ile Ser Glu
            595                 600
```

<210> SEQ ID NO 9
<211> LENGTH: 650
<212> TYPE: PRT
<213> ORGANISM: Cricetulus griseus

<400> SEQUENCE: 9

-continued

```
Met Leu Gln Glu Ala Gly Gly Gly Val Val Gly Ala Ala Gly Gly Gly
1               5               10              15

Ala Ala Thr Ala Glu Ala Pro Ala Gly Gly Asn Lys Met Ala Asp Phe
            20              25              30

Glu Glu Leu Arg Asn Met Val Ser Ser Phe Arg Val Ser Glu Leu Gln
        35              40              45

Val Leu Leu Gly Phe Ala Gly Arg Asn Lys Ser Gly Arg Lys His Asp
    50              55              60

Leu Leu Met Arg Ala Leu His Leu Leu Lys Ser Gly Cys Ser Pro Ala
65              70              75              80

Val Gln Ile Lys Ile Arg Glu Leu Tyr Arg Arg Arg Tyr Pro Arg Thr
                85              90              95

Leu Glu Gly Leu Ser Asp Leu Ser Thr Ile Lys Ser Ser Val Phe Ser
            100             105             110

Leu Asp Gly Ser Ser Ser Pro Val Glu Pro Asp Leu Ala Val Ala Gly
        115             120             125

Ile His Ser Leu Pro Ser Ser Ser Ile Thr Pro His Ser Pro Ser Ser
    130             135             140

Pro Val Gly Ser Val Leu Leu Gln Asp Ser Lys Pro Thr Phe Glu Met
145             150             155             160

Gln Gln Pro Ser Pro Pro Ile Pro Pro Val His Pro Asp Val Gln Leu
            165             170             175

Lys Asn Leu Pro Phe Tyr Asp Val Leu Asp Val Leu Ile Lys Pro Thr
            180             185             190

Ser Leu Val Gln Ser Ser Ile Gln Arg Phe Gln Glu Lys Phe Phe Ile
            195             200             205

Phe Ala Leu Thr Pro Gln Gln Val Arg Glu Ile Cys Ile Ser Arg Asp
    210             215             220

Phe Leu Pro Gly Gly Arg Arg Asp Tyr Thr Val Gln Val Gln Leu Arg
225             230             235             240

Leu Cys Leu Ala Glu Thr Ser Cys Pro Gln Glu Asp Asn Tyr Pro Asn
            245             250             255

Ser Leu Cys Ile Lys Val Asn Gly Lys Leu Phe Pro Leu Pro Gly Tyr
            260             265             270

Ala Pro Pro Pro Lys Asn Gly Ile Glu Gln Lys Arg Pro Gly Arg Pro
            275             280             285

Leu Asn Ile Thr Ser Leu Val Arg Leu Ser Ser Ala Val Pro Asn Gln
            290             295             300

Ile Ser Ile Ser Trp Ala Ser Glu Ile Gly Lys Asn Tyr Ser Met Ser
305             310             315             320

Val Tyr Leu Val Arg Gln Leu Thr Ser Ala Met Leu Leu Gln Arg Leu
            325             330             335

Lys Met Lys Gly Ile Arg Asn Pro Asp His Ser Arg Ala Leu Ile Lys
            340             345             350

Glu Lys Leu Thr Ala Asp Pro Asp Ser Glu Ile Ala Thr Thr Ser Leu
            355             360             365

Arg Val Ser Leu Met Cys Pro Leu Gly Lys Met Arg Leu Thr Ile Pro
    370             375             380

Cys Arg Ala Val Thr Cys Thr His Leu Gln Cys Phe Asp Ala Ala Leu
385             390             395             400

Tyr Leu Gln Met Asn Glu Lys Lys Pro Thr Trp Ile Cys Pro Val Cys
            405             410             415

Asp Lys Lys Ala Ala Tyr Glu Ser Leu Ile Leu Asp Gly Leu Phe Met
```

-continued

```
                420                425                430

Glu Ile Leu Asn Asp Cys Ser Asp Val Asp Glu Ile Lys Phe Gln Glu
        435                440                445

Asp Gly Ser Trp Cys Pro Met Arg Pro Lys Lys Glu Ala Met Lys Val
    450                455                460

Thr Ser Gln Pro Cys Thr Lys Ile Glu Ser Ser Ser Val Phe Ser Lys
465                470                475                480

Pro Cys Ser Val Ala Val Ala Ser Asp Ala Asn Lys Lys Lys Ile Asp
                485                490                495

Val Ile Asp Leu Thr Ile Glu Ser Ser Ser Asp Glu Glu Glu Asp Pro
            500                505                510

Pro Ala Lys Arg Lys Cys Ile Phe Met Ser Glu Thr Gln Ser Ser Pro
        515                520                525

Thr Lys Gly Val Leu Met Tyr Gln Pro Ser Ser Val Arg Val Pro Ser
        530                535                540

Val Thr Ser Val Asp Pro Ala Ala Ile Pro Pro Ser Leu Thr Asp Tyr
545                550                555                560

Ser Val Pro Phe His His Thr Pro Val Ser Ser Met Ser Ser Asp Leu
                565                570                575

Pro Gly Leu Asp Phe Leu Ser Leu Ile Pro Val Asp Pro Gln Gln Tyr
                580                585                590

Cys Pro Pro Met Phe Leu Asp Ser Leu Thr Ser Pro Leu Thr Ala Ser
        595                600                605

Ser Thr Ser Val Thr Thr Thr Ser Pro His Glu Ser Ser Thr His Val
        610                615                620

Ser Ser Ser Ser Ser Arg Ser Glu Thr Gly Val Ile Thr Ser Ser Gly
625                630                635                640

Ser Asn Ile Pro Asp Ile Ile Ser Leu Asp
                645                650

<210> SEQ ID NO 10
<211> LENGTH: 736
<212> TYPE: PRT
<213> ORGANISM: Cricetulus griseus

<400> SEQUENCE: 10

Met Asp Asp Leu Thr Leu Leu Asp Leu Leu Glu Cys Pro Val Cys Phe
1               5                  10                 15

Glu Lys Leu Asp Val Thr Ala Lys Val Leu Pro Cys Gln His Thr Phe
            20                 25                 30

Cys Lys Pro Cys Leu Gln Arg Ile Phe Lys Ala His Lys Glu Leu Arg
        35                 40                 45

Cys Pro Glu Cys Arg Thr Leu Val Phe Cys Ser Ile Glu Ala Leu Pro
    50                 55                 60

Ala Asn Leu Leu Leu Val Arg Leu Leu Asp Gly Val Arg Ser Gly Gln
65                 70                 75                 80

Asn Ser Trp Lys Arg Gly Ser Phe Arg Arg Pro Arg Ile Leu Thr Leu
                85                 90                 95

Gln Asp Ser Arg Lys Ser Lys Thr Ser Pro Arg Ser Leu Gln Ala Ser
            100                105                110

Pro Phe Arg Leu Val Pro Ser Val Arg Ile His Met Asp Gly Val Pro
        115                120                125

Arg Ala Lys Ala Leu Cys Asn Tyr Arg Gly Lys Asn Pro Gly Asp Leu
        130                135                140
```

-continued

```
Lys Phe Asn Lys Gly Asp Val Ile Leu Leu Arg Arg Gln Leu Asp Glu
145                 150                 155                 160

Asn Trp Tyr Gln Gly Glu Ile Asn Gly Val Ser Gly Ile Phe Pro Ala
                165                 170                 175

Ser Ser Val Glu Val Ile Lys Gln Leu Pro Gln Pro Pro Leu Cys
                180                 185                 190

Arg Ala Leu Tyr Asn Phe Asp Leu Arg Asp Lys Asp Lys Ser Glu Asn
                195                 200                 205

Gln Asp Cys Leu Thr Phe Leu Lys Asp Asp Ile Ile Thr Val Ile Ser
    210                 215                 220

Arg Val Asp Glu Asn Trp Ala Glu Gly Lys Leu Gly Asp Lys Val Gly
225                 230                 235                 240

Ile Phe Pro Ile Leu Phe Val Glu Pro Asn Leu Ala Ala Arg His Leu
                245                 250                 255

Leu Glu Arg Asn Lys Gly His Gln Leu Ser Arg Thr Lys Asn Leu Ser
                260                 265                 270

Leu Met Ser Ser Pro Ser Lys Gly Lys Ala Thr Asn Thr Ser Thr Leu
                275                 280                 285

Arg Lys Ser Pro Gly Ser Arg Arg Lys Gly Ser Gly Gln Phe Ser Ile
    290                 295                 300

Thr Thr Ala Leu Asn Thr Leu Asn Arg Met Val His Ser Pro Glu Gly
305                 310                 315                 320

His Gln Met Val Glu Ile Ser Thr Pro Val Leu Ile Ser Ser Thr Ser
                325                 330                 335

Pro Ser Val Phe Thr Gln His Gly Asp Lys Ala Asp Phe Pro Ala Asn
                340                 345                 350

Ser Ala Gly Gln Val Ser Thr Ser His Pro Ala Pro Ala Ser Pro Gly
                355                 360                 365

His Ser Thr Ala Met Val Ser Val Pro Ser Ser Gln Gln His Leu Ser
    370                 375                 380

Ala Asn Met Phe Val Ala Leu His Ser Tyr Ser Ala His Gly Pro Asn
385                 390                 395                 400

Glu Leu Asp Leu Gln Lys Gly Glu Gly Ile Lys Val Leu Gly Lys Tyr
                405                 410                 415

Gln Asp Gly Trp Leu Lys Gly Leu Ser Leu Val Thr Gly Arg Ala Gly
                420                 425                 430

Ile Phe Pro Ser Asp Tyr Val Ile Pro Val Phe Ser Ser Thr Ala Arg
                435                 440                 445

Lys Thr Ser Gly Phe Pro Asp Ser Arg Ser Pro Thr Val Tyr Thr Thr
    450                 455                 460

Trp Ala Leu Pro Thr Ser Ser Val Ser Ser Gln Gly Ser Phe Gln Glu
465                 470                 475                 480

Gly Asp Pro Trp Gln Ser Arg Pro Val Lys Ser Val Phe Val Pro Thr
                485                 490                 495

Ala Val Val Asn Pro Gln Gly Ser Thr Pro Gly Pro Gly Thr Ser Gly
                500                 505                 510

Gln Gly Ser Leu Arg Lys Ser Arg Ser Ile Met Arg Lys Asn Gly Ser
                515                 520                 525

Leu Gln Arg Pro Val Gln Ser Gly Ile Pro Thr Phe Met Leu Gly Ser
    530                 535                 540

Leu Arg His Ser Pro Thr Met Met Ile Gly Pro Gln Lys Phe His Phe
545                 550                 555                 560

Tyr Lys Pro Gln Gly Met Ala Ser Ser Pro Pro Pro Met Met Val Glu
```

-continued

```
           565                 570                 575

Met Gly Ser Lys Pro Ile Ser Thr Gly Glu Pro Ala Leu Thr Cys Ile
            580                 585                 590

Ser Arg Gly Ser Lys Thr Arg Ile His Ser Ala Ser Ser Ser Phe Ile
            595                 600                 605

Met Glu Gly Lys Glu Ile Pro Ile Lys Ser Glu Pro Pro Ser Lys Pro
        610                 615                 620

Pro Ala Ser Ala Pro Pro Ser Ile Leu Val Lys Pro Glu Asn Ser Lys
625                 630                 635                 640

Asn Gly Ile Glu Lys Gln Val Lys Thr Val Arg Phe Gln Asn Tyr Ser
                645                 650                 655

Pro Pro Pro Thr Lys His Tyr Ala Ser His Pro Thr Ser Gly Lys His
                660                 665                 670

Glu Gln Pro Ser Thr Leu Lys Gly Ser Gln Ser Glu Ala Lys His Thr
            675                 680                 685

Gly Ala Glu Met Thr Ile Leu Phe Ala His Arg Ser Gly Cys His Ser
        690                 695                 700

Gly Gln Gln Thr Asp Leu Arg Arg Lys Ser Ala Phe Gly Lys Thr Met
705                 710                 715                 720

Pro Pro Leu Ser Thr Thr Ser Gly Ser Gln Thr Ile Phe Thr Ser Gln
                725                 730                 735
```

CELLS HAVING GENE DUPLICATIONS AND USES THEREOF

REFERENCE TO SEQUENCE LISTING

This application is being filed electronically via EFS-Web and includes an electronically submitted sequence listing in .txt format. The .txt file contains a sequence listing entitled "PC072565A_SEQ_LISTING_ST25.txt" created on Jan. 26, 2023 and having a size of 42 KB. The sequence listing contained in this .txt file is part of the specification and is herein incorporated by reference in its entirety.

FIELD

The present invention relates to host cells for biologics production that have duplication of one or more genes, including methods for selecting, using, and making such cells. In certain embodiments, the cells are Chinese Hamster Ovary Cells (CHO) cells.

BACKGROUND

Large molecule biologics (e.g. recombinant proteins) are typically produced in cultured host cells, such has Chinese Hamster Ovary Cells (CHO) cells or human embryonic kidney (HEK) cells. While major advances have been made in recent decades in the development of improved host cells for biologics production, the generation and selection of specific host cells that have desirable growth and productivity characteristics has remained a time-consuming and challenging process.

Accordingly, there is a need for host cells having robust growth characteristics, and a need for methods of generating and selecting such cells.

SUMMARY

Provided herein are mammalian host cells having one or more gene duplications. Also provided are methods of selecting, using, and making such cells. In some aspects, cells having gene duplications provided herein have one or more improved growth characteristics as compared to otherwise identical cells that do not have the duplications.

In some embodiments, provided herein is a mammalian host cell comprising an exogenous nucleic acid and a duplication of at least one gene selected from the group consisting of: Spire1, Nars, Rps14, Smim3, Fem1c, Ppic, Lmnb1, Me2, Pias2, Sh3rf2, Rnmt, and Seh1l. Optionally, the host cell comprises duplication of at least two of the genes. Optionally, one of the two genes is selected from the group consisting of: Spire1, Nars, Rps14, Smim3, and at one of the two genes is selected from the group consisting of from the group consisting of: Fem1c, Ppic, Lmnb1, Me2, Pias2, and Sh3rf2. Optionally, the host cell has an improved growth characteristic as compared to an otherwise identical host cell lacking duplication of the gene or genes.

In some embodiments, provided herein is a mammalian host cell comprising an exogenous nucleic acid and a duplication of at least four genes; wherein one of the four genes is selected from the group consisting of: Spire1, Nars, Rps14, Smim3; wherein one of the four genes is selected from the group consisting of: Fem1c, Ppic, Lmnb1; wherein one of the four genes is selected from the group consisting of: Me2 and Pias2; and wherein one of the four genes is Sh3rf2. Optionally, the host cell has an improved growth characteristic as compared to an otherwise identical host cell lacking duplication of the genes.

In some embodiments, provided herein is a Chinese Hamster Ovary (CHO) host cell comprising an exogenous nucleic acid and a duplication of at least a portion of chromosome 2. Optionally, the duplicated portion of chromosome 2 comprises duplication of at least one, two, three, or four gene(s) selected from the group consisting of: Spire1, Nars, Rps14, Smim3, Fem1c, Ppic, Lmnb1, Me2, Pias2, and Sh3rf2. Optionally, the duplicated portion of chromosome 2 comprises duplication of at least four of the genes; wherein one of the four genes is selected from the group consisting of: Spire1, Nars, Rps14, Smim3; wherein one of the four genes is selected from the group consisting of: Fem1c, Ppic, Lmnb1; wherein one of the four genes is selected from the group consisting of: Me2 and Pias2; and wherein one of the four genes is Sh3rf2. Optionally, the host cell has an improved growth characteristic as compared to an otherwise identical host cell lacking duplication of the portion of chromosome 2.

In some embodiments, provided herein is a method of selecting a mammalian host cell having an improved growth characteristic, the method comprising: (a) assaying a mammalian host cell comprising an exogenous nucleic acid for duplication of at least one gene selected from the group consisting of: Spire1, Nars, Rps14, Smim3, Fem1c, Ppic, Lmnb1, Me2, Pias2, and Sh3rf2; and (b) selecting the mammalian host cell comprising duplication of the at least one gene, wherein the mammalian host cell comprising duplication of the at least one gene has an improved growth characteristic as compared to an otherwise identical mammalian host cell lacking duplication of the at least one gene. Optionally, the mammalian host cell is assayed for duplication of at least two of the genes. Optionally, one of the two genes is selected from the group consisting of: Spire1, Nars, Rps14, Smim3, and one of the two genes is selected from the group consisting of from the group consisting of: Fem1c, Ppic, Lmnb1, Me2, Pias2, and Sh3rf2.

In some embodiments, provided herein is a method for selecting a mammalian host cell having an improved growth characteristic, the method comprising: (a) assaying a mammalian host cell comprising an exogenous nucleic acid for duplication of at least four genes; (i) wherein one of the four genes is selected from the group consisting of: Spire1, Nars, Rps14, Smim3; (ii) wherein one of the four genes is selected from the group consisting of: Fem1c, Ppic, Lmnb1; (iii) wherein one of the four genes is selected from the group consisting of: Me2 and Pias2; and (iv) wherein one of the four genes is Sh3rf2; and (b) selecting the mammalian host cell comprising duplication of the at least four genes, wherein the mammalian host cell comprising duplication of the at least four genes has an improved growth characteristic as compared to an otherwise identical mammalian host cell lacking duplication of the at least four genes.

In some embodiments, provided herein is a method for producing a recombinant protein, the method comprising: (a) providing a recombinant mammalian host cell as provided herein, wherein the exogenous nucleic acid of the host cell of encodes a recombinant protein; and (b) culturing the recombinant mammalian host cell under conditions sufficient to express the recombinant protein. Optionally, the method further comprises recovering the expressed recombinant protein.

In some embodiments, provided herein is a method for producing a recombinant protein, the method comprising: (a) providing a recombinant mammalian host cell selected according to a method provided herein, wherein the exogenous nucleic acid of the host cell of encodes a recombinant protein; and (b) culturing the recombinant mammalian host cell under conditions sufficient to express the recombinant protein. Optionally, the method further comprises recovering the expressed recombinant protein.

In some embodiments, in a host cell or method provided herein comprising an exogenous nucleic acid, the exogenous nucleic acid encodes a protein. Optionally, the protein is a therapeutic protein. Optionally, the therapeutic protein is an antibody or a cytokine.

In some embodiments, provided herein is a method of preparing a mammalian host cell having an improved growth characteristic, the method comprising: introducing an exogenous nucleic acid molecule comprising the sequence of least one gene selected from the group consisting of: Spire1, Nars, Rps14, Smim3, Fem1c, Ppic, Lmnb1, Me2, Pias2, and Sh3rf2 into the mammalian host cell; wherein the host cell comprising the exogenous nucleic acid molecule has an improved growth characteristic as compared to an otherwise identical mammalian host cell that does not contain the exogenous nucleic acid molecule. Optionally, one or more exogenous nucleic acid molecules comprising the sequence of least two of the genes are introduced into the host cell. Optionally, one of the two genes is selected from the group consisting of: Spire1, Nars, Rps14, Smim3, and one of the two genes is selected from the group consisting of: Fem1c, Ppic, Lmnb1, Me2, Pias2, and Sh3rf2. Optionally, the sequences of at least four of the genes are introduced into the host cell, wherein one of the four genes is selected from the group consisting of: Spire1, Nars, Rps14, Smim3; wherein one of the four genes is selected from the group consisting of: Fem1c, Ppic, Lmnb1; wherein one of the four genes is selected from the group consisting of: Me2 and Pias2; and wherein one of the four genes is Sh3rf2.

In some embodiments, in a host cell or method provided herein, the mammalian cell is a mouse cell, a rat cell, a Chinese Hamster Ovary (CHO) cell, or a human cell. Optionally, the human cell is a HEK cell, a HeLa cell, or a HT1080 cell.

In some embodiments, in a host cell or method provided herein, the host cell is a Chinese Hamster Ovary (CHO) cell.

In some embodiments, in a host cell or method provided herein, the exogenous nucleic acid is chromosomally-integrated in a host cell chromosome. Optionally, the host cell chromosome contains a recombination target site for site-specific integration of the exogenous nucleic acid into the chromosome.

In some embodiments, in a host cell or method provided herein, the improved growth characteristic is greater cell count, greater viable cell count, greater cell density, or greater viable cell density of a first cell culture comprising the cell having an improved growth characteristic as compared to a second cell culture comprising an otherwise identical mammalian host cell lacking duplication of the gene(s) or portion of chromosome 2, wherein the first and second cell cultures are grown under the same conditions and for the same time period. Optionally, the time period is 3, 5, 7, or 10 days. Optionally, the greater cell count, greater viable cell count, greater cell density, or greater viable cell density is an increase of the respective value in the first cell culture by least 10%, 25%, 50%, 75%, 100%, or 200% as compared to the value in the second cell culture. Optionally, the cell count, viable cell count, cell density, or viable cell density is measured by an automated cell analyzer.

In some embodiments, in a method provided herein comprising assaying a host cell for duplication of a gene(s), the method comprises determining a relative amount of DNA comprising the sequence of the gene or mRNA transcribed from the gene.

In some embodiments, provided herein is a recombinant protein prepared according to a method provided herein, by a host cell provided herein, by a host cell selected according to a method provided herein, by a host cell prepared according to a method provided herein, or according to a host cell or method provided herein.

In some embodiments, in a host cell, method, or recombinant protein provided herein, the Spire1 gene encodes a polypeptide that is at least 70%, at least 80%, at least 90%, at least 95%, at least 97%, at least 99%, or 100% identical to the amino acid sequence as shown in SEQ ID NO: 1; the Nars gene encodes a polypeptide that is at least 70%, at least 80%, at least 90%, at least 95%, at least 97%, at least 99%, or 100% identical to the amino acid sequence as shown in SEQ ID NO: 2; the Rps14 gene encodes a polypeptide that is at least 70%, at least 80%, at least 90%, at least 95%, at least 97%, at least 99%, or 100% identical to the amino acid sequence as shown in SEQ ID NO: 3; the Smim3 gene encodes a polypeptide that is at least 70%, at least 80%, at least 90%, at least 95%, at least 97%, at least 99%, or 100% identical to the amino acid sequence as shown in SEQ ID NO: 4; the Fem1c gene encodes a polypeptide that is at least 70%, at least 80%, at least 90%, at least 95%, at least 97%, at least 99%, or 100% identical to the amino acid sequence as shown in SEQ ID NO: 5; the Ppic gene encodes a polypeptide that is at least 70%, at least 80%, at least 90%, at least 95%, at least 97%, at least 99%, or 100% identical to the amino acid sequence as shown in SEQ ID NO: 6; the Lmnb1 gene encodes a polypeptide that is at least 70%, at least 80%, at least 90%, at least 95%, at least 97%, at least 99%, or 100% identical to the amino acid sequence as shown in SEQ ID NO: 7; the Me2 gene encodes a polypeptide that is at least 70%, at least 80%, at least 90%, at least 95%, at least 97%, at least 99%, or 100% identical to the amino acid sequence as shown in SEQ ID NO: 8: the Pias2 gene encodes a polypeptide that is at least 70%, at least 80%, at least 90%, at least 95%, at least 97%, at least 99%, or 100% identical to the amino acid sequence as shown in SEQ ID NO: 9; or the Sh3rf2 gene encodes a polypeptide that is at least 70%, at least 80%, at least 90%, at least 95%, at least 97%, at least 99%, or 100% identical to the amino acid sequence as shown in SEQ ID NO: 10.

5

Figure 1A:
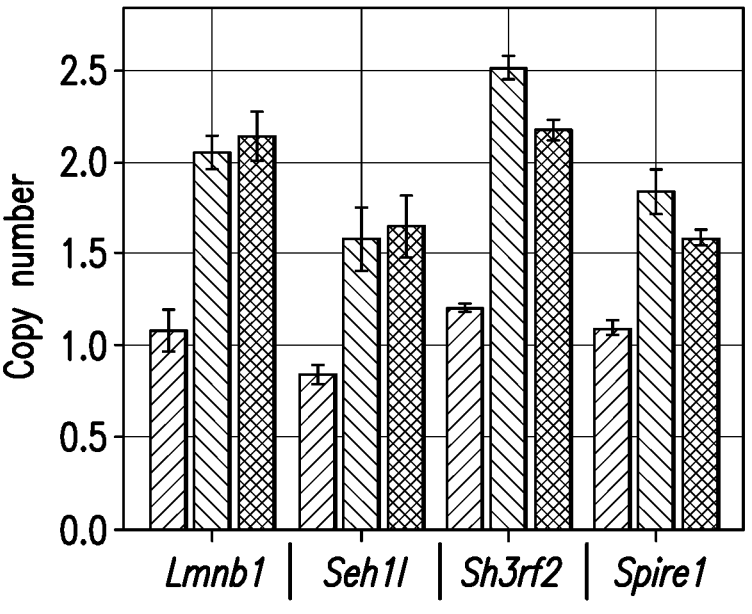
FIG. 1A depicts a bar graph showing gene copy number analysis for the genes Lmnb1, Seh1l, Sh3rf2, and Spire1 in the clonal cell lines T3-6 25 gen, T3-6 100 gen, and T3-9 25 gen. The X axis lists the respective gene, and the Y axis lists the average gene copy number. For each gene, three bars shown. In order from left to right, the three bars show the average gene copy number for the respective gene per chromosome 2 in T3-6 25 gen, T3-6 100 gen, and T3-9 25 gen cell lines, respectively.

T3-9 25 gen cell lines. (The T3-6 25 gen value was assigned "1"; the T3-6 100 gen and T3-9 25 gen values are relative to the T3-6 25 gen value.)

DETAILED DESCRIPTION

Disclosed herein are mammalian host cells having one or more gene duplications, and related methods and compositions, such as methods of selecting, using, and making such cells, and compositions for preparing such cells.

The invention provided herein relates to the finding that host cells that have duplication of one or more of the genes Spire1, Nars, Rps14, Smim3, Fem1c, Ppic, Lmnb1, Me2, Pias2, Sh3rf2, Rnmt, and Seh1l have improved growth characteristics as compared to corresponding host cells that do not have duplication of one or more of these genes.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995), as well as in subsequent editions and corresponding websites of the above references, as applicable.

Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

The following terms, unless otherwise indicated, shall be understood to have the following meanings:

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', F(ab')$_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$ and IgA$_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

The terms "polypeptide", "oligopeptide", "peptide" and "protein" are used interchangeably herein to refer to chains of amino acids of any length. The chain may be linear or branched, it may comprise modified amino acids, and/or may be interrupted by non-amino acids. The terms also encompass an amino acid chain that has been modified naturally or by intervention: for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

As known in the art, "polynucleotide," or "nucleic acid," as used interchangeably herein, refer to chains of nucleotides of any length and conformation (e.g. linear or circular) and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, a "recombinant" nucleic acid refers to a nucleic acid molecule that contains a polynucleotide sequence that does not occur in nature and/or or which is synthetically manufactured. For example, a "recombinant" nucleic acid may contain a protein-encoding gene coupled to a vector sequence. The sequence of the protein-encoding gene may occur in nature, but the gene does not naturally occur in combination with the vector sequence. Put another way, a "recombinant" nucleic acid molecule may contain as part of the molecule a nucleic acid sequence that occurs in nature, but that sequence is either coupled to another sequence (such that the totality of the nucleic acid molecule sequence does not occur in nature) and/or the molecule is synthetically manufactured. A "recombinant" polypeptide refers to a polypeptide produced from a recombinant nucleic acid.

As used herein, an "exogenous" nucleic acid refers to a recombinant nucleic acid molecule that will be or has been introduced into a host cell (e. g. by conventional genetic engineering methods, preferably by means of transformation, electroporation, lipofection, or transfection), which was prior to said introduction was not present in said host cell. In some circumstances, an exogenous nucleic acid contains a nucleotide sequence that does not naturally occur in the host cell. Such sequences are also termed "transgenic". In some circumstances, an exogenous nucleic acid may contain a nucleotide sequence of that is the same as a sequence that is endogenous to the cell (e.g. an exogenous nucleic acid molecule may contain a nucleotide sequence of a gene that is endogenous to the host cell, such that introduction of the exogenous nucleic acid molecule into the host cell introduces an additional copy of the gene into the host cell). An "exogenous nucleic acid" refers to an exogenous nucleic acid molecule, or the nucleotide sequence thereof.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting. The term "or" when used in the context of a listing of multiple options (e.g. "A, B, or C") shall be interpreted to include any one or more of the options, unless the context clearly dictates otherwise. It is understood that wherever embodiments are described herein with the language "comprising," otherwise analogous embodiments described in terms of "consisting of" and/or "consisting essentially of" are also provided.

Exemplary methods and materials are described herein, although methods and materials similar or equivalent to those described herein can also be used in the practice or testing of the present invention. The materials, methods, and examples are illustrative only and not intended to be limiting.

Cells Having Duplications of One or More Genes

In one aspect, provided herein are mammalian host cells having one or more gene duplications. The genes include, for example, Spire1, Nars, Rps14, Smim3, Fem1c, Ppic, Lmnb1, Me2, Pias2, Sh3rf2, Rnmt, and Seh1l. Also provided herein are Chinese Hamster Ovary (CHO) cells having a duplication of one or more portions of CHO chromosome 2.

As used herein "duplication" of a gene refers to a situation where one or more additional copies of the gene are present in a cell than normally occur in a cell (i.e. than are present in a cell having a wild-type number of copies of the gene.) For example, if ordinarily one copy of gene XYZ is present per chromosome 5 in a wild-type cell, then gene XYZ is "duplicated" in a cell if two, three, four or more copies of the gene are present per chromosome 5 in the cell. In some situations, a duplicated gene is present in average amount per cell in a culture of a cell line having the duplication of interest that is at least 1.5, 1.6, 1.7, 1.8, 1.9, 2, 2.5, 3, 3.5, or 5 times greater than the amount present per cell in a culture of a corresponding cell having a wild-type number of copies of the gene. Similarly, a duplication of a portion of a chromosome refers to a situation where one or more additional copies of a portion of a chromosome are present in a cell than normally occur in a cell. As described further elsewhere herein, cells having a duplicated gene or portion of a chromosome of interest may be generated by various methods including, for example, introduction of an exogenous nucleic acid containing the gene to be duplicated into the cell, or by selection of a modified recombinant host cell containing the duplicated gene.

Embodiments provided herein may include a Spire1 gene. The Spire1 gene encodes the protein Spire homolog 1. Spire1 is an actin nucleation factor. Exemplary Spire1 gene and polypeptide sequences are provided via UniProt Accession Nos. Q52KF3 (mouse), Q08AE8 (human), and D3ZEX7 (rat). An exemplary Chinese hamster (*Cricetulus griseus*) Spire1 mRNA sequence is provided under NCBI accession number XM_027402695.1 and polypeptide sequence is shown in SEQ ID NO: 1 in Table 1.

Embodiments provided herein may include a Nars gene. The Nars gene encodes the protein asparagine-tRNA ligase, cytoplasmic (also known as Nars1 or NRS). Nars catalyzes the attachment of asparagine to tRNA(Asn). Exemplary Nars gene and polypeptide sequences are provided via UniProt Accession Nos. Q8BP47 (mouse), O43776 (human), and F1LPV0 (rat). An exemplary Chinese hamster (*Cricetulus griseus*) Nars mRNA sequence is provided under NCBI accession number XM_016974175.1 and polypeptide sequence is shown in SEQ ID NO: 2 in Table 1.

Embodiments provided herein may include a Rps14 gene. The Rps14 gene encodes the 40S ribosomal protein S14. Exemplary Rps14 gene and polypeptide sequences are provided via UniProt Accession Nos. P62264 (mouse), P62263 (human), and P13471 (rat). An exemplary Chinese hamster (*Cricetulus griseus*) Rps14 mRNA sequence is provided under NCBI accession number NM_001244519.1 and polypeptide sequence is shown in SEQ ID NO: 3 in Table 1.

Embodiments provided herein may include a Smim3 gene. The Smim3 gene encodes the small integral membrane protein 3. Exemplary Smim3 gene and polypeptide sequences are provided via UniProt Accession Nos. Q99PE5 (mouse), Q9BZL3 (human), and Q99PE6 (rat). An exemplary Chinese hamster (*Cricetulus griseus*) Smim3 mRNA sequence is provided under NCBI accession number XM_027439246.1 and polypeptide sequence is shown in SEQ ID NO: 4 in Table 1.

Embodiments provided herein may include a Fem1c gene. The Fem1c gene encodes the protein fem-1 homolog C. Fem1c is a probable component of an E3 ubiquitin-protein ligase complex. Exemplary Fem1c gene and polypeptide sequences are provided via UniProt Accession Nos. Q8CEF1 (mouse), Q96JP0 (human), and D3ZZR4 (rat). An exemplary Chinese hamster (*Cricetulus griseus*) Fem1c mRNA sequence is provided under NCBI accession number XM_003506780.4 and polypeptide sequence is shown in SEQ ID NO: 5 in Table 1.

Embodiments provided herein may include a Ppic gene. The Ppic gene encodes the protein peptidyl-prolyl cis-trans isomerase C. Ppic catalyzes cis-trans isomerization of proline imidic peptide bonds in peptides. Exemplary Ppic gene and polypeptide sequences are provided via UniProt Accession Nos. P30412 (mouse), P45877 (human), and Q6AYQ9 (rat). An exemplary Chinese hamster (*Cricetulus griseus*) Ppic mRNA sequence is provided under NCBI accession number XM_007644661.2 and polypeptide sequence is shown in SEQ ID NO: 6 in Table 1.

Embodiments provided herein may include a Lmnb1 gene. The Lmnb1 gene encodes the protein lamin-B1. Lamin-B1 is part of the nuclear lamina. Exemplary Lmnb1 gene and polypeptide sequences are provided via UniProt Accession Nos. P14733 (mouse), P20700 (human), and P70615 (rat). An exemplary Chinese hamster (*Cricetulus griseus*) Lmnb1 mRNA sequence is provided under NCBI accession number XM_007623862.2 and polypeptide sequence is shown in SEQ ID NO: 7 in Table 1.

Embodiments provided herein may include a Me2 gene. The Me2 gene encodes the protein NAD-dependent malic enzyme, mitochondrial (also known as malic enzyme 2). Exemplary Me2 gene and polypeptide sequences are provided via UniProt Accession Nos. Q99KE1 (mouse) and P23368 (human). An exemplary Chinese hamster (*Cricetulus griseus*) Me2 mRNA sequence is provided under NCBI accession number XM_003506799.2 and polypeptide sequence is shown in SEQ ID NO: 8 in Table 1.

Embodiments provided herein may include a Pias2 gene. The Pias2 gene encodes the protein E3 SUMO-protein ligase PIAS2 (also known as protein inhibitor of activated STAT2). Exemplary Pias2 gene and polypeptide sequences are provided via UniProt Accession Nos. Q8C5D8 (mouse), O75928 (human), and Q6AZ28 (rat). An exemplary Chinese hamster (*Cricetulus griseus*) Pias2 mRNA sequence is provided under NCBI accession number XM_027397933.1 and polypeptide sequence is shown in SEQ ID NO: 9 in Table 1.

Embodiments provided herein may include a Sh3rf2 gene. The Sh3rf2 gene encodes the protein E3 ubiquitin-protein ligase SH3RF2 (also known as SH3 domaining containing ring finger 2). Exemplary Sh3rf2 gene and polypeptide sequences are provided via UniProt Accession Nos. Q8BZT2 (mouse), Q8TEC5 (human), and Q498M5 (rat). An exemplary Chinese hamster (*Cricetulus griseus*) Sh3rf2 mRNA sequence is provided under NCBI accession number XM_003503277.4 and polypeptide sequence is shown in SEQ ID NO: 10 in Table 1.

TABLE 1

| Description | Sequence |
| --- | --- |
| Spire1 amino acid (*Cricetulus griseus*) | MAQPSSPGGEGPQFGATGDSRDALSLEEILRLYNQPINEEQAWAVCFQCCGSLRATA ARRQPHRRVRSAAQIRVWRDGAVTLAPAAGEEGEPPPASGKLGYSHCTETEVIESLGI IYKALDYGLKENEERELSPPLEQLIDQMANTVEADGNSDEGYEAADEGPEDEDGGKR NISAIRSYQDVMKICAAHLPAESEAPNHYQAVCRALFAETMELHTFLTKIKSAKENLKKI QEMEKTDESSTDLEDLKNADWARFWVQVMRDLRNGVKLKKVQQRQYNPLPIEYQLT PYEMLMDDIRCRRYTLRKVMVNGDIPPRLRKSAHEIILDFIRSRPPLNPASARKLKPTPP RPRSLHERILEEIKAERKLRPVSPEEIRRSKLDVTTPDSSKNVGESSMVNGGLASQTKE NGLGAAQPGPAQRKKLLKAPTLAELDSSDSEEETLHKSTSSSSASPSLYEDPVLEAMC TRKKPPKFLPISSTPQPERRQPPQRRHSIEKETPTNVRQFLPPSRQSSRSLVPRITSVW PRTPFRPLFSTIQTASLLSSHPFEAAMFGVAGAMYYLFERAFTSRWKPSKEEFCYPVE CLALTVEEVMHIRQVLVKAELEKYQQYKDVYTALKKGKLCFCCRTRRFSFFTWSYTCQ FCKRPVCSQCCKKMRLPSKPYSTLPIFSLGPSALQRGESCPRPEKSSTAHHRPLRSIA RFSSKSKSVDKSDEELQFPKEFMEDWSTMEVCVDCKKFISEIISSSRRSLVLANKRARL KRKTQSFYMSSAGPSEYCPSERTINEI (SEQ ID NO: 1) |

TABLE 1-continued

| Description | Sequence |
| --- | --- |
| Nars amino acid (*Cricetulus griseus*) | MSSEVIRATAGMVLAELYVSDREGNDATGDGTKEKPFKTGLKALMTVGKEPFPTIYVD<br>SQKENERWDVISKSQMKNIKKMWHREQMKNDSREKKEAEDNLRREKNLEEAKKIIIKN<br>DPSLPEPACVKICALEGYRGQRVKVFGWVHRLLREGKNLMFLVLRDGTGYLQCVLSD<br>DLCQCYNGVVLSTESSVAVYGTLNLTPKGKQAPGGHELSCDFWELVGLAPAGGADNL<br>INEESDVDVQLNNRHMMIRGENMSKILKARSMITRCFRDHFFDRGYCEVTTPTLVQTQ<br>VEGGATLFKLDYFGEEAFLTQSSQLYLETCLPALGDVFCIAQSYRAEQSRTRRHLAEFT<br>HVEAECPFLTFEDLLNRLEDLVCDVVDRVLKSPVASIVYDLNPNFKPPKRPFRRMNYS<br>DAIEWLREHDVKKEDGTLYEFGDDIPEAPERLMTDTINEPILLCRFPVEIKSFYMQRCPE<br>DPRLTESVDVLMPNVGEIVGGSMRSWDSEEILEGYKREGIDPAPYYWYTDQRKYGTC<br>PHGGYGLGLERFLSWILNRYHIRDVCLYPRFVQRCRP (SEQ ID NO: 2) |
| Rps14 amino acid (*Cricetulus griseus*) | MAPRKGKEKKEEQVISLGPQVAEGENVFGVCHIFASFNDTFVHVTDLSGKETICRVTG<br>GMKVKADRDESSPYAAMLAAQDVAQRCKELGITALHIKLRATGGNRTKTPGPGAQSAL<br>RALARSGMKIGRIEDVTPIPSDSTRRKGGRRGRRL (SEQ ID NO: 3) |
| Smim3 amino acid (*Cricetulus griseus*) | MDAISQSPVDVLLPKHILDIWAIVLIILATIVIMTSLFLCPATAVIIYRMRTHPVLNGAV<br>(SEQ ID NO: 4) |
| Fem1c amino acid (*Cricetulus griseus*) | MDLKTAVFNAARDGKLRLLTKLLASKSKEEVSSLISEKTNGATPLLMAARYGHLOMVEF<br>LLEQCSASIEVGGSVNFDGETIEGAPPLWAASAAGHLKVVQSLLNHGASVNNTTLTNS<br>TPLRAACFDGHLEIVKYLVEHKADLEVSNRHGHTCLMISCYKGHKEIAQYLLEKGADVN<br>RKSVKGNTALHDCAESGSLDIMKMLLMYCAKMEKDGYGMTPLLSASVTGHTNIVDFLT<br>HHAQTSKTERINALELLGATFVDKKRDLLGALKYWKKAMNMRYSDRTNIISKPVPQTLI<br>MAYDYAKEVNSAEELEGLIADPDEMRMQALLIRERILGPSHPDTSYYIRYRGAVYAD<br>SGNFKRCINLWKYALDMQQSNLDPLSPMTASSLLSFAELFSFMLQDRAKGLLGTTVTF<br>DDLMGILCKSVLEIERAIKQTQCPADPLQLNKALSIILHLICLLEKVPCTLEQDHFKKQTIY<br>RFLKLHPRGKNNFSPLHLAVDKNTTCVGRYPVCKFPSLQVTAILIECGADVNVRDSDD<br>NSPLHIAALNNHPDIMNLLIKSGAHFDATNLHKQTASDLLDEKEIAKNLIQPINHITLQCLA<br>ARVIVNHRIYYKGNIPEKLETFVSLHR (SEQ ID NO: 5) |
| Ppic amino acid (*Cricetulus griseus*) | MIPGPRLLLPAVLCLGLGTLVSSSGSSGVRKRGPSVTAKVFFDVKIGDKDVGRIVIGLFG<br>KVVPKTVENFVALATGEKGYGYKGSIFHRVIKDFMIQGGDFTARDGTGGMSIYGETFP<br>DENFKLKHYGIGWVSMANAGPDTNGSQFFITLTKPSWLDGKHVVFGKVLDGMTVVHSI<br>ELQATDDHDRPFTDCTIVNSGKIDVKTPFVVEVPDW (SEQ ID NO: 6) |
| Lmnb1 amino acid (*Cricetulus griseus*) | MKLREYEAALNSKDAALATALGDKKSLEGDLEDLKDQIAQLEASLSAAKKQLADETLLK<br>VDLENRCQSLTEDLEFRKNMYEEEINETRRKHETRLVEVDSGRQIEYEYKLAQALHEM<br>REQHDAQVRLYKEELEQTYHAKLENARLSSEMNTSTVNSAREELMESRMRIESLSSQL<br>SNLQKESRACLEKIQELEDMLAKEKDNSRRMLSDKEREMAEIRDQMQQQLNDYEQLL<br>DVKLALDMEISAYRKLLEGEEERLKLSPSPSSRVTVSRASSSRSVRTTRGKRKRVDVE<br>ESEASSSVSISHSASATGNVCIEEIDVDGKFIRLKNTSEQDQPMGGWEMIRKIGDTSVS<br>YKYTSRYVLKAGQTVTIWAANAGVTASPPTDLIWKNQNSWGTGEDVKVILKNSQGEEV<br>AQRSTVFKTTIPEEEEEEEEEPIGVVIEEERFHQQGAPRASNRSCAIM (SEQ ID NO: 7) |
| Me2 amino acid (*Cricetulus griseus*) | MAGGRHKPPSASSWNRVREKMFSRVRAIVTPCTLTCRHLHLKEKGKPLMLNPRTNKG<br>MAFTLQERQMLGLQGLLPPKIETQDIQALRFHRNLKKMTSPLEKYIYIMGIQERNEKLFY<br>RILQDDIESLMPIVYTPTVGLACSQYGHIFRRPKGLFISISDRGHVRSIVDNWPENHVKA<br>VVVTDGERILGLGDLGVYGMGIPVGKLCLYTACAGIQPEKCLPVCIDVGTDNKALLKDP<br>FYMGLYQKRDRSQLYDDLIDEFMKAITDRYGRNTLIQFEDFGNHNAFRFLRKYREKYC<br>TFNDDIQGTAAVALSGLLATQKVINKPVSEHKILFLGAGEAALGIANLIVMSMVESGLSE<br>EEARRKVWMFDKNGLLVKGRSASIDSNQEPFAHGAPENVPGTFEDAVNKLKPSVIIGV<br>AGAGRLFTPGVIKAMASINERPIIFALSNPTAQAECTAEEAYTLTEGRCLFASGSPFEPV<br>KLQDGRVFTPGQGNNAYIFPGVALAVILCQTRHISDSVFLEAAKALTSQLTDEELAQGR<br>LYPSLANIQEVSVNIAIKVTEYLYANKMAFRYPEPEDKAKYVKERIWRSDYVSLLPDVYD<br>WPESSLKPPQISE (SEQ ID NO: 8) |
| Pias2 amino acid (*Cricetulus griseus*) | MLQEAGGGVVGAAGGGAATAEAPAGGNKMADFEELRNMVSSFRVSELQVLLGFAGR<br>NKSGRKHDLLMRALHLLKSGCSPAVQIKIRELYRRRYPRTLEGLSDLSTIKSSVFSLDG<br>SSSPVEPDLAVAGIHSLPSSSITPHSPSSPVGSVLLQDSKPTFEMQQPSPPIPPVHPDV<br>QLKNLPFYDVLDVLIKPTSLVQSSIQRFQEKFFIFALTPQQVREICISRDFLPGGRRDYTV<br>QVQLRLCLAETSCPQEDNYPNSLCIKVNGKLFPLPGYAPPPKNGIEQKRPGRPLNITSL<br>VRLSSAVPNQISISWASEIGKNYSMSVYLVRQLTSAMLLQRLKMKGIRNPDHSRALIKE<br>KLTADPDSEIATTSLRVSLMCPLGKMRLTIPCRAVTCTHLQCFDAALYLQMNEKKPTWI<br>CPVCDKKAAYESLILDGLFMEILNDCSDVDEIKFQEDGSWCPMRPKKEAMKVTSQPCT<br>KIESSSVFSKPCSVAVASDANKKKIDVIDLTIESSSDEEEDPPAKRKCIFMSETQSSPTK<br>GVLMYQPSSVRVPSVTSVDPAAIPPSLTDYSVPFHHTPVSSMSSDLPGLDFLSLIPVDP<br>QQYCPPMFLDSLTSPLTASSTSVTTTSPHESSTHVSSSSSRSETGVITSSGSNIPDIISL<br>D (SEQ ID NO: 9) |
| Sh3rf2 amino acid (*Cricetulus griseus*) | MDDLTLLDLLECPVCFEKLDVTAKVLPCQHTFCKPCLQRIFKAHKELRCPECRTLVFCSI<br>EALPANLLLVRLLDGVRSGQNSWKRGSFRRPRILTLQDSRKSKTSPRSLQASPFRLVP<br>SVRIHMDGVPRAKALCNYRGKNPGDLKFNKGDVILLRRQLDENWYQGEINGVSGIFPA<br>SSVEVIKQLPQPPPLCRALYNFDLRDKDKSENQDCLTFLKDDIITVISRVDENWAEGKL<br>GDKVGIFPILFVEPNLAARHLLERNKGHQLSRTKNLSLMSSPSKGKATNTSTLRKSPGS<br>RRKGSGQFSITTALNTLNRMVHSPEGHQMVEISTPVLISSTSPSVFTQHGDKADFPAN |

TABLE 1-continued

| Description | Sequence |
|---|---|
| | SAGQVSTSHPAPASPGHSTAMVSVPSSQQHLSANMFVALHSYSAHGPNELDLQKGE |
| | GIKVLGKYQDGWLKGLSLVTGRAGIFPSDYVIPVFSSTARKTSGFPDSRSPTVYTTWAL |
| | PTSSVSSQGSFQEGDPWQSRPVKSVFVPTAVVNPQGSTPGPGTSGQGSLRKSRSIM |
| | RKNGSLQRPVQSGIPTFMLGSLRHSPTMMIGPQKFHFYKPQGMASSPPPMMVEMGS |
| | KPISTGEPALTCISRGSKTRIHSASSSFIMEGKEIPIKSEPPSKPPASAPPSILVKPENSKN |
| | GIEKQVKTVRFQNYSPPPTKHYASHPTSGKHEQPSTLKGSQSEAKHTGAEMTILFAHR |
| | SGCHSGQQTDLRRKSAFGKTMPPLSTTSGSQTIFTSQ (SEQ ID NO: 10). |

In some embodiments, provided herein is a host CHO cell having a duplication of a portion of CHO chromosome 2. Specific portions of CHO chromosome 2 that may be duplicated in host cells provided here having improved growth characteristics are described in Examples 2 and 3. As discussed in Example 3, the genes Spire1, Nars, Rps14 and Smim3 are in CHO chromosome 2 scaffold region NW_020822466.1, the genes Fem1c, Ppic and Lmnb1 are in CHO chromosome 2 scaffold region NW_020822459.1, the genes Me2 and Pias2 are in CHO chromosome 2 scaffold region NW_020822440.1, and the gene Sh3rf2 is in CHO chromosome 2 scaffold region NW_020822442.1.

Cells Having Improved Growth Characteristics

In one aspect, provided herein are mammalian host cells having one or more improved growth characteristics. For example, cells that have a duplication of one or more of the genes Spire1, Nars, Rps14, Smim3, Fem1c, Ppic, Lmnb1, Me2, Pias2, Sh3rf2, Rnmt, and Seh1l have one or more improved growth characteristics as compared to host cells that do not have duplication of one or more of these genes. Also provided herein are CHO cells which have a duplication of a portion of CHO chromosome 2 that have one or more improved growth characteristics as compared to host cells that do not have duplication of the portion of CHO chromosome 2.

As used herein, "growth characteristic" refers to a feature of a cell or cell culture that is correlated with cell growth. Cell growth may be assessed by measuring, for example, A) cell count (also known as "cell number"), B) cell viability; C) cell metabolism, D) cell size, or combinations thereof. Frequently, multiple aspects of a cell culture are examined at the same time when assessing cell growth. For example, cultured cells are commonly assessed for "viable cell density", which takes into account both the number of cells and viability of cells in a cell culture. In addition, cell growth may be assessed by measuring any of the above parameters over a period of time. For example, cell growth can be assessed by measuring the time it takes for the number of cells in a culture to double in number (i.e. "doubling time").

Cells may be counted manually (e.g. with a hemocytometer), or via an automated instrument. Automated cell counter instruments include, for example, Cedex HiRes System (Roche), LUNAm (Logos Biosystem), Nova FLEX analyzer (Nova Biomedical), CELLOMETER™ Auto T4Cell Viability Counter (Peqlab), TC10™ and TC20™ (Bio-Rad), COUNTESS® Automated Cell Counter (Invitrogen), and VI-CELL® Cell Viability Analyzer (Beckman Coulter). Cells can also be counted in automated bioreactor systems [e.g. AMBR (Sartorius)] that contain an integrated cell counter. Collectively, automated cell counter and bioreactor systems may be referred to herein as "cell analyzers".

Viable cells can be identified by various methods known in the art. For example, viable cells can be identified by exposing cells to a dye that selectively binds either living or dead cells. Dyes that stain dead cells but not living cells include trypan blue, eosin, and propidium. The membrane of living cells exclude these dyes, but dead cell membranes do not exclude the dyes. Additional dyes that can be used to assess cell viability include, for example, dyes that bind to DNA (e.g. ethidium monoazide) or to phosphatidylserine (e.g., Annexin V).

Cell viability can also be exampled via assays in which living cells convert a substrate to a product that can be readily detected (such as a colored or fluorescent product). In these assays, the amount of detectable product generated is proportional to the viability of the assayed cells. Representative assays include, for example tetrazolium reduction assays [e.g. CellTiter 96® Non-Radioactive Cell Proliferation Assay (Promega); Cell Growth Determination Kit (Sigma-Aldrich); MTT Cell Growth Assay Kit (Millipore); CellTiter 96® D Aqueous One Solution Cell Proliferation Assay (Promega); In Vitro Toxicology Assay Kit, XTT (Sigma-Aldrich); Cell Counting Kit-8, WST-8 based (Dojindo Molecular Technologies)], resazurin reduction assays [e.g. CELLTITER-BLUE® Cell Viability Assay (Promega); In Vitro Toxicology Assay Kit, Resazurin (Sigma-Aldrich)], protease substrate assays [e.g. using substrate glycylphenyl-alanyl-aminofluourocoumarin (GF-AFC); CELLTITER-FLUOR™ Cell Viability Assay (Promega)]; ATP/luciferase assays [e.g. CELLTITER-GLO® Luminescent Cell Viability Assay (Promega); ATPLITE™ 1 Step (Perkin Elmer); ATP Bioluminescent Cell Assay Kit (Sigma-Aldrich)]

Cell metabolism can examine, for example, DNA synthesis in cells (e.g. BrdU assay or EdU assay) or nuclear proteins associated with cellular proliferation (e.g. anti-Ki67 antibodies).

Multiple aspects of cell cultures can be examined simultaneously. For example, in some embodiments, cell analyzers can determine multiple parameters including the number of cells and cell viability (i.e. to determine the number of viable cells). For example, the automated VI-CELL™ Cell Viability Analyzer (Beckman Coulter) uses trypan blue staining for identification of viable cells, and provides automated measurements of, for example, cell number, cell size, percent viability, total cell density, and viable cell density. In another example, the AMBR® (Sartorius) bioreactor system can combine a bioreactor for culturing multiple cell cultures with sensors and a cell analyzer for evaluating multiple features of the cell cultures, including cell count, cell viability, and metabolites (lactate, glucose, etc.). In another example, the Cell Viability Imaging kit (Sigma) includes reagents for simultaneous staining of viable, dead, and total cells in a sample, using calcein-AM, propidium iodide, and Hoeschst 33342 dyes, respectively.

A cell or cell culture that has an "improved growth characteristic" (or the like) as compared to a reference cell or cell culture will have a greater value (or, where appropriate, a smaller value, where the smaller value indicates faster growth) for at least one, two, three, or four of the above characteristics (i.e. cell number, cell viability, cell metabolism, cell size, or related characteristic) than the reference cell or cell culture over which it has an "improved growth characteristic". In some embodiments, a cell or cell culture that has an "improved growth characteristic" than a reference cell or cell culture will have a total cell count or a viable cell count which is at least about 10%, 20%, 25% 30%, 40%, 50%, 60%, 70%, 80%, 90%, 100%, 100%, 200%, 300%, or 500% greater than the reference cell or cell culture, when the cells are cultured under the same conditions for the same period of time. In some embodiments, a cell or cell culture that has an "improved growth characteristic" than a reference cell or cell culture will have a total cell density or a viable cell density which is at least about 10%, 20%, 25% 30%, 40%, 50%, 60%, 70%, 80%, 90%, 100%, 100%, 200%, 300%, or 500% greater than the reference cell or cell culture, when the cells are cultured under the same conditions for the same period of time. In some embodiments, a cell or cell culture that has an "improved growth characteristic" than a reference cell or cell culture will have a doubling time which is at least about 10%, 20%, 30%, 40%, 50%, 60%, 70%, 80%, or 90% less than the reference cell or cell culture (i.e. the cell or cell culture with the improved growth characteristic doubles in less time than the reference cell or cell culture), when the cells are cultured under the same conditions for the same period of time. In some embodiments, a cell or cell culture that has an "improved growth characteristic" than a reference cell or cell culture will have a BrdU, Edu, or Ki67 signal amount which is at least about 10%, 20%, 25% 30%, 40%, 50%, 60%, 70%, 80%, 90%, 100%, 100%, 200%, 300%, or 500% greater than the reference cell or cell culture, when the cells are cultured under the same conditions for the same period of time.

Nucleic Acids

In some embodiments, provided herein are nucleic acids. Nucleic acids can have various components and formats as described below.

In some embodiments, a cell provided herein (e.g. a host cell having duplication of one or more of the genes Spire1, Nars, Rps14, Smim3, Fem1c, Ppic, Lmnb1, Me2, Pias2, Sh3rf2, Rnmt, and Seh1l) may contain a nucleotide sequence of interest. As used herein, a "nucleotide sequence of interest" refers to any nucleotide sequence that a person may want to introduce into a host cell or have present in a vector. A nucleotide sequence of interest may be in an exogenous nucleic acid. Most commonly, a nucleotide sequence of interest is a DNA sequence that encodes a polypeptide of interest or that is a template for the generation of an RNA molecule of interest. However, a nucleotide sequence of interest may alternatively, for example, be a sequence which provides a regulatory or structural function (e.g. a promoter or enhancer sequence), or which serves a different purpose, such as a restriction enzyme sequence for cloning purposes (e.g. a nucleotide sequence of interest may be a multiple cloning site). A nucleotide sequence of interest may be of any nucleotide length. A nucleotide sequence of interest may be a DNA sequence or an RNA sequence. In some embodiments, a nucleotide sequence of interest is a sequence that is not endogenously present in the host cell. In some embodiments, a nucleotide sequence of interest is separately endogenously present in the host cell (i.e. the sequence is also present in the host cell separate from a recombinant nucleic acid construct containing the nucleotide sequence of interest introduced into the host cell). In such embodiments, the nucleotide sequence of interest may be introduced into a host cell, for example, if there is relatively low expression of the corresponding endogenous nucleotide sequence, and it is desirable to have increased expression of the nucleotide sequence in the cell.

In some embodiments, a nucleotide sequence of interest encodes a recombinant protein (also referred to herein as a "recombinant polypeptide" or "polypeptide of interest"). Polypeptides of interest include, for example, an antibody, an enzyme, a peptide hormone, a fusion protein, or a detectable protein (e.g. a fluorescent protein such as a green fluorescent protein). In some embodiments, a polypeptide of interest may be a structurally or functionally defined part of a polypeptide, for instance, a fragment of an antibody, such as a heavy chain, light chain, or constant region of an antibody, or a catalytic domain of an enzyme. As understood by a person of skill in the art, a polypeptide may be of more than one of the types mentioned above (e.g. an enzyme may also be a detectable protein, etc.).

In some embodiments, a nucleotide sequence of interest is a DNA template for an RNA molecule of interest. RNA molecules of interest include, for example, CRISPR-cas9 system related RNA, or RNAi (interfering RNA)-related molecules such as miRNA, siRNA, or shRNA.

In some aspects, provided herein are nucleic acid constructs. A "nucleic acid construct" as provided herein is a type of polynucleotide or nucleic acid described above. A "nucleic acid construct" may have any of the characteristics of a polynucleotide or nucleic acid described above. Typically, a "nucleic acid construct" as provided herein contains two or more functional units within the chain of nucleotides that make up the polynucleotide. A functional unit in a nucleotide sequence may be any type of discrete nucleotide sequence having a particular function such as, for example, a nucleotide sequence of interest, a gene encoding a polypeptide, a regulatory sequence, a recombination sequence, or a template for an inhibitory RNA molecule.

A "recombination target sequence" or a "recombination target site" is a stretch of nucleotides being necessary for and allowing, together with a recombinase, a targeted recombination and defining the location of such a recombination. As used herein, "recombination target sequence" is typically used to refer to a recombination sequence on an exogenous nucleic acid construct to be introduced into a host cell, and "recombination target site" is typically used to refer to a corresponding recombination sequence in a host cell chromosome. A recombination target site may be non-native to a host cell genome (e.g. it may be introduced into a host cell chromosome as part of a landing pad sequence).

In some embodiments, one or more recombination target sequences may be included in a nucleic acid construct provided herein, so that some or all of the nucleic acid construct may be integrated into a corresponding site at in a host cell chromosome.

Any suitable recombination target site, target sequence and recombinase combination may be used with the compositions and methods provided herein, including both tyrosine recombinase and serine recombinase-based systems. Recombinases (and their corresponding recombination target sequences) that may be used with nucleic acid constructs and host cells provided herein include, for example, Cre, Dre, Flp, KD, B2, B3, λ, HK022, HP1, γδ, ParA, Tn3, Gin, Bxb1, φC31, φBT1, and R4. Site specific recombinases are described, for example, in Turan and Bode, *The FASEB Journal,* 25 (12): 4088-107 (2011); Nem et al, PNAS, 108 (34): 14198-203 (2011); and Xu et al, BMC Biotechnology, 13 (87) (2013).

In some embodiments, a nucleotide sequence of interest (e.g. a gene encoding a polypeptide of interest) in a nucleic acid construct may be linked to one or more regulatory genetic control elements in the nucleic acid construct. In certain embodiments, a genetic control element directs constitutive expression of the nucleotide sequence of interest. In certain embodiments, a genetic control element that provides inducible expression of a nucleotide sequence of interest can be used. The use of an inducible genetic control element (e.g., an inducible promoter) allows for modulation of the production of, for example, a polypeptide encoded by a gene. Non-limiting examples of potentially useful inducible genetic control elements for use in eukaryotic cells include hormone-regulated elements (e.g., see Mader, S. and White, J. H., *Proc. Natl. Acad. Sci. USA* 90:5603-5607, 1993), synthetic ligand-regulated elements (see, e.g. Spencer, D. M. et al., *Science* 262:1019-1024, 1993) and ionizing radiation-regulated elements (e.g., see Manome, Y. et al., *Biochemistry* 32:10607-10613, 1993; Datta, R. et al., *Proc. Natl. Acad. Sci. USA* 89:10149-10153, 1992). Additional cell-specific or other regulatory systems known in the art may be used in accordance with the methods and compositions provided herein.

In some aspects, provided herein is a vector containing a nucleic acid construct. The nucleic acid construct may have any of the characteristics as described elsewhere herein.

In some embodiments a vector contains one or more of a promoter sequence, a directional cloning site, a non-directional cloning site, a restriction site, an epitope tag, a polyadenylation sequence, and antibiotic resistance gene. In some embodiments the promoter sequence is Human cytomegalovirus immediate early promoter, the directional cloning site is TOPO, the epitope tag is V5 for detection using anti-V5 antibodies, the polyadenylation sequence is from Herpes Simplex Virus thymidine kinase, and antibiotic resistance gene for is blasticidin, puromycin, or geneticin (G418).

In some embodiments provided herein, recombinant nucleic acid sequences such as promoter sequences, a directional cloning sites, sequences encoding epitope tags, polyadenylation sequences, antibiotic resistance genes, and protein coding genes may be part of both nucleic acid constructs and vectors.

In some embodiments, a vector provided herein is an expression vector. Expression vectors generally are replicable polynucleotide constructs that contain a recombinant nucleic acid construct. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

Polynucleotides provided herein may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials. Polynucleotides complementary to any nucleic acid construct or vector sequences provided herein are also encompassed by the present invention. It will be appreciated by those of ordinary skill in the art that, as a result of the degeneracy of the genetic code, there may be multiple nucleotide sequences that encode a polypeptide provided herein.

Homology analysis of polynucleotide or polypeptide sequences may be performed using methods known in the art (e.g. BLAST). Comparisons between two sequences are typically performed by comparing the sequences over a comparison window to identify and compare local regions of sequence similarity. Preferably, percent homology or sequence identity is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Polynucleotides provided herein can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g. without limitation, pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Host Cells

As used herein, the term "host cell", refers to a cell or cell culture harboring a recombinant nucleic acid provided herein, or that can be a recipient for such nucleic acids. Host cells include progeny of a single host cell.

In some embodiments, a host cell may harbor a recombinant nucleic acid stably integrated at a location in its genome (e.g. in a chromosome). In some embodiments, a recombinant nucleic acid in a host cell is not stably integrated into the host cell's genome—e.g. the recombinant nucleic acid may be in the host cell in a plasmid.

In the context of the present disclosure, a "cell" is preferably a mammalian cell. A mammalian cell may be, for example, a canine cell (e.g. Madin-Darby canine kidney epithelial (MDCK) cell), a primate cell, a human cell (e.g. human embryonic kidney (HEK) cell), a mouse cell or a hamster cell. In some embodiments, a hamster cell is a Chinese hamster ovary (CHO) cell. Optionally, a CHO cell may be a CHOK1, a CHOK1 SV cell (Porter, A J et al. Biotechnol Prog. 26 (2010), 1455-1464), or another strain of CHO cell. In some embodiments, a mammalian cell is a BALB/c mouse myeloma cell, a human retinoblast cell (PER.C6), a monkey kidney cell, a human embryonic kidney cell (293), a baby hamster kidney cell (BHK), a mouse sertoli cell, an African green monkey kidney cell (CERO-76), a HeLa cell, a buffalo rat liver cell, a human lung cell, a human liver cell, a mouse mammary tumor cell, a TRI cell, a MRC 5 cell, a FS4 cell, or a human hepatoma cell (e.g. Hep G2). In some embodiments, a cell is a non-mammalian cell (e.g. an insect cell or a yeast cell).

In some embodiments, provided herein are host cells that contain a recombinant nucleic acid that contains a nucleotide sequence of interest, and which have a duplication of one or more of the genes Spire1, Nars, Rps14, Smim3, Fem1c, Ppic, Lmnb1, Me2, Pias2, Sh3rf2, Rnmt, and Seh11. Also are provided herein are related compositions and methods of making the cells.

In some embodiments, provided herein are host cells that have received one or more nucleic acid constructs that contain one or more of the Spire1, Nars, Rps14, Smim3, Fem1c, Ppic, Lmnb1, Me2, Pias2, Sh3rf2, Rnmt, and Seh11 genes.

In some additional aspects, also provided herein are host cells that have not received one or more exogenous Spire1, Nars, Rps14, Smim3, Fem1c, Ppic, Lmnb1, Me2, Pias2, Sh3rf2, Rnmt, and Seh11 genes, but which have been genetically modified such that their endogenous Spire1, Nars, Rps14, Smim3, Fem1c, Ppic, Lmnb1, Me2, Pias2, Sh3rf2, Rnmt, or Seh11 genes have higher expression than in corresponding non-modified cells. For example, in some embodiments, a recombinant promoter sequence may be introduced into a host cell genome such that, once it is introduced, it is operably linked to the endogenous Spire1, Nars, Rps14, Smim3, Fem1c, Ppic, Lmnb1, Me2, Pias2, Sh3rf2, Rnmt, or Seh11 gene, and causes increased expression of the respective endogenous Spire1, Nars, Rps14, Smim3, Fem1c, Ppic, Lmnb1, Me2, Pias2, Sh3rf2, Rnmt, or Seh11 gene.

Introduction of Polynucleotides into Cells

Polynucleotides provided herein (e.g. nucleic acid constructs, vectors, etc.) can be introduced into a host cell by any of a number of appropriate means, including, for example, electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of method for introduction of a polynucleotide into a host cell will often depend on features of the host cell.

Methods suitable for introducing nucleic acids sufficient to achieve expression of a protein of interest into mammalian host cells are known in the art. See, for example, Gething et al., *Nature*, 293:620-625, 1981; Mantei et al., *Nature*, 281:40-46, 1979; Levinson et al. EP 117,060; and EP 117,058, each of which is incorporated herein by reference. For mammalian cells, common methods of introducing genetic material into mammalian cells include the calcium phosphate precipitation method of Graham and van der Erb (*Virology*, 52:456-457, 1978) or the Lipofectamine™ (Gibco BRL) method of Hawley-Nelson (Focus 15:73, 1993). General aspects of mammalian cell host system transformations have been described by Axel in U.S. Pat. No. 4,399,216 issued Aug. 16, 1983. For various techniques for introducing genetic material into mammalian cells, see Keown et al., *Methods in Enzymology*, 1989, Keown et al., *Methods in Enzymology*, 185:527-537, 1990, and Mansour et al., *Nature*, 336:348-352, 1988. Additional methods suitable for introducing nucleic acids include electroporation, for example as employed using the GenePulser XCell™ electroporator by BioRad™ or Neon Electroporation by ThermoFisher. Non-limiting representative examples of suitable vectors for expression of proteins in mammalian cells include pCDNA1; pCD, see Okayama, et al. Mol. Cell Biol. 5:1136-1142, 1985; pMClneo Poly-A, see Thomas, et al. Cell 51:503-512, 1987; a baculovirus vector such as pAC 373 or pAC 610; CDM8, see Seed, B. Nature 329:840, 1987; and pMT2PC, see Kaufman, et al. EMBO J. 6:187-195, 1987, each of which is incorporated herein by reference in its entirety.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 1992, 3:147); ligand-linked DNA (see, e.g., Wu, J. Biol. Chem., 1989, 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes.

Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 1994, 14:2411, and in Woffendin, Proc. Natl. Acad. Sci., 1994, 91:1581. Naked DNA can be introduced into cells by forming a precipitate containing the DNA and calcium phosphate. Alternatively, naked DNA can also be introduced into cells by forming a mixture of the DNA and DEAE-dextran and incubating the mixture with the cells or by incubating the cells and the DNA together in an appropriate buffer and subjecting the cells to a high-voltage electric pulse (e.g., by electroporation). Naked DNA can also be directly injected into cells by, for example, microinjection. Alternatively, naked DNA can also be introduced into cells by complexing the DNA to a cation, such as polylysine, which is coupled to a ligand for a cell-surface receptor (see for example Wu, G. and Wu, C. H. J. Biol. Chem. 263: 14621, 1988; Wilson et al. J. Biol. Chem. 267:963-967, 1992; and U.S. Pat. No. 5,166,320, each of which is hereby incorporated by reference in its entirety). Binding of the DNA-ligand complex to the receptor facilitates uptake of the DNA by receptor-mediated endocytosis.

In certain embodiments, a polynucleotide provided herein is stably introduced into a host cell. In certain embodiments, a polynucleotide provided herein is transiently introduced into the host cell.

Integration of Nucleic Acids into Host Cell Chromosomes

In embodiments provided herein in which a polynucleotide is stably introduced into a host cell (for example, in situations where the polynucleotide is integrated into a host cell chromosome), the polynucleotide may be randomly integrated into a chromosome in the host cell, or the polynucleotide may be integrated at a specific location in a chromosome in the host cell. These approaches may be referred herein to as a "random integration" or "site-specific integration ("SSI")", respectively.

For random integration, typically, one or more recombinant nucleic acid constructs are prepared in which the recombinant nucleic acid construct(s) each contain at least one nucleotide sequence of interest and at least one selectable marker (e.g. a gene encoding antibiotic resistance). For example, a nucleic acid construct can be prepared that contains one or more of the genes Spire1, Nars, Rps14, Smim3, Fem1c, Ppic, Lmnb1, Me2, Pias2, Sh3rf2, Rnmt, and Seh11, and a selectable marker. In some embodiments, a first nucleic acid construct is prepared that contains one or more of the genes Spire1, Nars, Rps14, Smim3, Fem1c, Ppic, Lmnb1, Me2, Pias2, Sh3rf2, Rnmt, and Seh11, and a second nucleic acid construct is prepared that contains one or more of the genes Spire1, Nars, Rps14, Smim3, Fem1c, Ppic, Lmnb1, Me2, Pias2, Sh3rf2, Rnmt, and Seh11, where the genes in the first construct are different than in the second construct.

After preparation of the polynucleotide(s) containing one or more of the genes Spire1, Nars, Rps14, Smim3, Fem1c, Ppic, Lmnb1, Me2, Pias2, Sh3rf2, Rnmt, and Seh11, the polynucleotides can be introduced into host cells. Host cells that have taken up the polynucleotides can be selected, for example, by resistance to the antibiotic for which the antibiotic resistance gene in the construct provides resistance. Generally, after polynucleotide(s) containing the genes of interest are introduced into a population of cells, and cells are selected for via the relevant selectable marker system (e.g. antibiotic resistance) there may be a heterogeneous population of cells (also referred to herein as a "pool" of cells) containing different numbers of copies of the polynucleotide(s) containing the one or more Spire1, Nars, Rps14, Smim3, Fem1c, Ppic, Lmnb1, Me2, Pias2, Sh3rf2, Rnmt, and Seh11 genes, as well as different locations of integration of the polynucleotide(s) in chromosomes in the cell. Optionally, individual cells from this pool of cells may be sorted and isolated, and individual homogenous cell line populations of different cells may be established (also referred to herein as cell line "clones"). Alternatively, in some embodiments, a heterogeneous pool of cells containing one or more exogenous Spire1, Nars, Rps14, Smim3, Fem1c, Ppic, Lmnb1, Me2, Pias2, Sh3rf2, Rnmt, and Seh11 genes may be maintained. Either type of cell population described above (e.g. homogenous or heterogeneous populations) may be used for various methods (e.g. protein production) as described herein.

In some embodiments, nucleic acid constructs for random integration may be linear polynucleotides. In some embodiments, the linear structure may be generated by synthesis of a linear molecule (e.g. by PCR or chemical polynucleotide synthesis). In some embodiments, the linear structure may be generated by cleavage of a circular vector (e.g. by a restriction enzyme) to generate a linear nucleic acid molecule.

In some embodiments, provided herein is a host cell comprising one or more nucleic acid constructs provided herein integrated into a chromosome of the cell. For example, in some embodiments, provided herein is a host cell comprising a recombinant nucleic acid construct comprising a nucleotide sequence of interest and or more of the genes Spire1, Nars, Rps14, Smim3, Fem1c, Ppic, Lmnb1, Me2, Pias2, Sh3rf2, Rnmt, or Seh11 integrated into a chromosome of the cell.

For site-specific integration, in some embodiments, a host cell that contains a "landing pad" at a defined chromosomal locus is used. The landing pad contains an exogenous nucleotide sequence that contains one or more recombination target sites, which is stably integrated into a chromosome. When an exogenous nucleic acid construct that contains one or more recombination target sequences that correspond to the recombination target site in the landing pad is introduced into the host cell, an expression cassette in the exogenous nucleic acid construct may be integrated into or replace the landing pad sequence (for example, via recombinase mediated cassette exchange (RMCE)). In some embodiments, a site-specific integration system may be used as described in, for example, Zhang L, et. al, Biotechnology Progress, 31(6): 1645-1656, 13 Oct. 2015, Inniss, M, et al, Biotechnology Bioengineering, 114(8): 1837-1846, 14 Mar. 2017, or International Publication WO 2013/190032, which are hereby incorporated by reference for all purposes.

In some embodiments, a landing pad in a host cell line may be located at a "hot-spot" in the host cell's genome. As used herein, the term "hot-spot" means a site, in the genome of a host cell which provides for a stable and high expression of a gene or genes integrated at the site.

A cell that contains a landing pad for SSI may also be referred to herein as a "SSI host cell". As used herein, "SSI host cell" refers to a host cell that contains an exogenous nucleotide sequence that includes at least one recombination target site (e.g. a landing pad). The recombination target site in the host cell permits site specific integration of exogenous nucleotide sequences into the genome of the host cell, thus enabling a predetermined localized and directed integration of desired nucleotide sequences at a desired place in a host cell's genome. Thus, in some embodiments, a site specific integration host cell is capable of targeted integration of a recombinant nucleic acid construct (or an expression cassette therein) described herein into a chromosome of the host cell. In some embodiments, a site specific integration host cell is capable of targeted integration of an expression cassette by recombination mediated cassette exchange (RMCE).

For compositions and methods provided herein involving recombination of an exogenous nucleic acid construct into a host cell genome, as described above, a recombinase is also present or introduced into the host cell. Methods provided herein involving introducing an exogenous nucleic acid construct may include introducing a gene encoding a recombinase into the host cell.

In some embodiments, provided herein is a host cell comprising an exogenous recombinant nucleic acid construct integrated into a specific location in a chromosome in the cell. The nucleic acid construct may have any of the properties of a nucleic acid construct provided herein.

Recombinant Proteins

In another aspect, provided herein are recombinant proteins (also referred to herein as "recombinant polypeptides") that are produced via the compositions and methods provided herein. For example, provided herein is a recombinant protein that is encoded by a nucleotide sequence of interest that is a component of a recombinant nucleic acid construct provided herein.

Any polypeptide that is expressible in a host cell may be produced in accordance with the present teachings and may be produced according to the methods of the invention or by the cells of the invention. The polypeptide may have an amino acid sequence that occurs in nature, or may alternatively have a sequence that was engineered or selected by humans.

Polypeptides that may desirably be expressed in accordance with the present invention will often be selected on the basis of an interesting or useful biological or chemical activity. For example, the present invention may be employed to express any pharmaceutically or commercially relevant enzyme, receptor, antibody, hormone, regulatory factor, antigen, binding agent, etc. In some embodiments, the protein expressed by cells in culture are selected from antibodies, or fragments thereof, nanobodies, single domain antibodies, glycoproteins, therapeutic proteins, growth factors, clotting factors, cytokines, fusion proteins, pharmaceutical drug substances, vaccines, or enzymes. One of ordinary skill in the art will understand that any protein may be expressed in accordance with the present invention.

Isolation of the Expressed Protein

In general, it will typically be desirable to isolate and/or purify proteins expressed according to the present invention. In certain embodiments, the expressed protein is secreted into the medium and thus cells and other solids may be removed, as by centrifugation or filtering for example, as a first step in the purification process. Alternatively, the expressed protein may remain in the cell or may be bound to the surface of the host cell. In such circumstances, the media may be removed and the host cells expressing the protein are lysed as a first step in the purification process. Lysis of mammalian host cells can be achieved by any number of means well known to those of ordinary skill in the art, including physical disruption by glass beads and exposure to high pH conditions.

The expressed protein may be isolated and purified by standard methods including, but not limited to, chromatography (e.g., ion exchange, affinity, size exclusion, and hydroxyapatite chromatography), gel filtration, centrifugation, or differential solubility, ethanol precipitation and/or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol. 182), Academic Press, 1997, each of which is incorporated herein by reference). For immunoaffinity chromatography in particular, the protein may be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin may be added at any or all stages in order to reduce or eliminate degradation of the protein during the purification process. Protease inhibitors are particularly advantageous when cells must be lysed in order to isolate and purify the expressed protein.

Cell Cultures and Cell Culture Media

The terms "medium", "media", and the like as used herein refer to a solution containing components or nutrients which nourish growing mammalian cells. Typically, the nutrients include essential and non-essential amino acids, vitamins, energy sources, lipids, and trace elements required by the cell for minimal growth and/or survival. Such a solution may also contain further nutrients or supplementary components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), inorganic compounds present at high final concentrations, amino acids, lipids, and/or glucose or other energy source. In some embodiments, a medium is advantageously formulated to a pH and salt concentration optimal for cell survival and proliferation. In some embodiments, a medium is a feed medium that is added after the beginning of the cell culture.

A wide variety of mammalian growth media may be used in accordance with the present invention. In some embodiments, cells may be grown in one of a variety of chemically defined media, wherein the components of the media are both known and controlled. In some embodiments, cells may be grown in a complex medium, in which not all components of the medium are known and/or controlled.

Chemically defined growth media for mammalian cell culture have been extensively developed and published over the last several decades. All components of defined media are well characterized, and so defined media do not contain complex additives such as serum or hydrolysates. Early media formulations were developed to permit cell growth and maintenance of viability with little or no concern for protein production. More recently, media formulations have been developed with the express purpose of supporting highly productive recombinant protein producing cell cultures. Such media are preferred for use in the method of the invention. Such media generally comprises high amounts of nutrients and in particular of amino acids to support the growth and/or the maintenance of cells at high density. If necessary, these media can be modified by the skilled person for use in the method of the invention. For example, the skilled person may decrease the amount of phenylalanine, tyrosine, tryptophan and/or methionine in these media for their use as base media or feed media in a method as disclosed herein.

In some embodiments, methods and compositions provided herein involve cell cultures and cell culture media. The terms "culture" and "cell culture" as used herein refer to a cell population that is in a medium under conditions suitable to survival and/or growth of the cell population. As will be clear to those of ordinary skill in the art, in some embodiments, these terms as used herein refer to the combination comprising the cell population and the medium in which the population is present. In some embodiments, the cells of the cell culture comprise mammalian cells. In some embodiments, a cell culture comprises cells in suspension. In some embodiments, a cell culture comprises cells grown on a substrate.

In some embodiments, host cells provided herein which contain a recombinant nucleic acid construct provided herein may be used to produce a protein encoded by a nucleotide sequence of interest. Similarly, as provided herein, methods and compositions provided herein may be used to obtain host cells that contain a nucleotide sequence of interest, and polypeptides encoded by such nucleotide sequences of interest may be produced and purified. In addition, such host cells may be generated and cultured.

The present invention may be used with any cell culture method that is amenable to the desired process (e.g., introduction of a recombinant nucleic acid construct according to methods provided herein and production of a recombinant protein (e.g., an antibody)). As a non-limiting example, cells may be grown in batch or fed-batch cultures, where the culture is terminated after sufficient expression of the recombinant protein (e.g., antibody), after which the expressed protein (e.g., antibody) is harvested. Alternatively, as another non-limiting example, cells may be grown in batch-refeed, where the culture is not terminated and new nutrients and other components are periodically or continuously added to the culture, during which the expressed recombinant protein (e.g., antibody) is harvested periodically or continuously. Other suitable methods (e.g., spin-tube cultures) are known in the art and can be used to practice the present invention.

In some embodiments, provided herein are compositions containing polypeptides produced from host cells and according to methods provided herein, and one or more pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Methods

In some aspects, provided herein are methods of selecting host cells provided herein, methods for preparing host cells provided herein, and methods for producing recombinant proteins provided herein.

In some embodiments, host cells having duplication of one or more of the genes Spire1, Nars, Rps14, Smim3, Fem1c, Ppic, Lmnb1, Me2, Pias2, and Sh3rf2 may be selected by assaying cells for duplication of at least one of these genes. Methods for identifying gene copy number in a cell are known in the art. For example gene copy number can be determined via fluorescent in situ hybridization (FISH), comparative genomic hybridization, microarray-based systems, whole exome sequencing, and whole genome sequencing. See, e.g. Zare, F. et al, BMC Bioinformatics 18, 286 (2017).

In some embodiments, host cells having duplication of one or more of the genes Spire1, Nars, Rps14, Smim3, Fem1c, Ppic, Lmnb1, Me2, Pias2, and Sh3rf2 may be selected by assaying cells for mRNA expression from these genes. Relative RNA expression levels may provide an indication of the copy number of the corresponding gene. RNA expression can be analyzed by methods known in the art, such as quantitative PCR, microarrays, RNA sequencing (including whole transcriptome sequencing). See, e.g. Soneson C and Delorenzi M, BMC Bioinformatics, 14, 91 (2013).

In some embodiments, host cells that have previously been transfected with an exogenous nucleic acid comprising a nucleotide sequence of interest can be assayed for duplication of one or more of the genes Spire1, Nars, Rps14, Smim3, Fem1c, Ppic, Lmnb1, Me2, Pias2, Sh3rf2, Rnmt, and Seh1l, or of a portion of CHO chromosome 2. Cells that contain such duplications can then be selected further analysis and/or use in downstream processes.

In some embodiments, host cells having duplication of one or more of the genes Spire1, Nars, Rps14, Smim3, Fem1c, Ppic, Lmnb1, Me2, Pias2, Sh3rf2, Rnmt, and Seh1l, can be prepared by processes described herein for preparing nucleic acids, and introducing such nucleic acids into host cells.

In some embodiments, provided herein are methods for producing recombinant proteins. According to such methods, cells provided herein (including cells selected according to methods provided herein or prepared according to methods provided herein) can be used, for example, for the expression of a recombinant protein encoded by an exogenous nucleic acid in a host cell.

In some embodiments, compositions and methods provided herein may be used in combination with compositions and methods disclosed in PCT/IB2016/055666, which is hereby incorporated by reference for all purposes.

One of ordinary skill in the art will appreciate that the exact purification technique will vary depending on the character of the protein to be purified, the character of the cells from which the protein is expressed, and/or the composition of the medium in which the cells were grown.

Incorporated by reference herein for all purposes is the content of U.S. Provisional Patent Application No. 62/706, 075 (filed Jul. 30, 2020).

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1: Identification of Different Clonal Cell Populations from the Same Parental Cell Line that have Different Growth Characteristics In this example, distinct clonal cell populations that are derived from the same parental cell line were identified. The clonal cell populations have different growth characteristics despite being derived from the same parental cell line.

Example 1a: Clones from Parental Cell Line CHO Cell Line 1 Containing mAb1

In-house Pfizer host CHO Cell Line 1 (a CHOK1 derivative) was transfected with a polynucleotide encoding a monoclonal antibody ("mAb1"), to establish a cell line that stably expresses the mAb1, referred to in this Example as "parental cell line CHO1".

From parental cell line CHO1, three separate clonal cell line populations were established: "T3-6", "T3-9", and "T3-11". The three clonal cell lines were treated identically and were not genetically manipulated as compared to the parental cell line CHO1. All three clonal cell lines were passaged twice weekly in CD CHO medium (ThermoFischer/Gibco) for generation accrual. Cryopreserved banks were established at 25 generation (25 gen) and 100 generations (100 gen) for all three cell lines.

In order to assess the phenotypic stability of the clonal cell lines "T3-6", "T3-9", and "T3-11", cryopreserved cells from the 25 gen and 100 gen cryopreserved banks were thawed simultaneously and passaged three times under identical culture conditions prior to being cultured in a standard fed batch cell culture process using AMBR® bioreactor system (Sartorius).

Growth data for the different clonal cell lines from the 25 gen and 100 gen cryopreserved banks is shown below in Table 2. Day 0 is the date of the initiation of the cell culture. As shown in the Table, the peak viable cell density of the T3-6 25 gen was significantly lower than that of T3-9 and T3-11 at 25 gen. For example, on day 7, the T3-6 25 gen clonal cells had a viable cell density (VCD) of $178.16 \times 10^5$/ml, whereas the T3-9 gen and T3-11 gen had a VCD of $296.775 \times 10^5$/ml and $289.175 \times 10^5$/ml, respectively. At generation 100, the peak cell density of T3-6 100 gen increased to the level comparable to that of T3-9 and T3-11 at 25 gen whereas no growth changes detected between 25 gen and 100 gen for cell lines T3-9 and T3-11.

TABLE 2

Viable Cell Density (VCD) of T3-6, T3-9, and T3-11 clonal cell lines from 25 gen and 100 gen cryopreserved banks at different days of culture

| Clone: | Viable Cell Density (VCD) ($10^5$ cells/ml) | | | | | |
|---|---|---|---|---|---|---|
| Gene- | T3-6 | | T3-9 | | T3-11 | |
| ration: | 25gen | 100gen | 25gen | 100gen | 25gen | 100gen |
| Day 0 | 17.35 | 19.84 | 17.16 | 19.805 | 17.93 | 21.71 |
| Day 3 | 100.29 | 138.06 | 129.055 | 127.435 | 122.34 | 129.51 |
| Day 5 | 182.08 | 280.37 | 304.595 | 268.58 | 287.31 | 251.795 |
| Day 7 | 178.16 | 308.76 | 296.775 | 301.025 | 289.175 | 298.055 |
| Day 10 | 109.9 | 224.965 | 216.51 | 205.655 | 238.26 | 207.39 |
| Day 12 | 71.6 | 203.42 | 139.035 | 146.42 | 178.635 | 170.265 |

Example 1b: Clones from Parental Cell Line: CHO 2 Containing mAb2

In-house Pfizer host CHO Cell Line 2 (a CHOK1 derivative) was transfected with a polynucleotide encoding a monoclonal antibody ("mAb2"), to establish a cell line that stably expresses the mAb2, referred to in this Example as "parental cell line CHO2"

From the parental cell line CHO2, two separate clonal cell line populations were established: "C15" and "C32". The two clonal cell lines were treated identically and were not genetically manipulated as compared to the parental cell line CHO2. At the same generational age, the C15 and C32 clonal cell populations were separately grown (each in triplicate in 3 separate vessels) in a standard fed batch cell culture process using AMBR® bioreactor system (Sartorius).

Growth data for the C15 and C32 clonal cell lines is shown below in Table 3. Day 0 is the initiation of the cell culture. As shown in Table 3, the peak cell VCD of the C32 population was significantly lower than that of C15 from day 3 onward. For example, on day 7, the each of the C15 cultures (i.e. in each vessel) had a VCD between $290-310 \times 10^5$/ml, whereas each of the C32 cultures only had a VCD between $100-110 \times 10^5$/ml.

TABLE 3

Viable Cell Density (VCD) of C15 and C32 clonal cell lines at different days of culture

| | Viable Cell Density ($10^5$ cells/ml) | | | | | |
|---|---|---|---|---|---|---|
| | C15 | | | C32 | | |
| | Vessel #1 | Vessel #2 | Vessel #3 | Vessel #1 | Vessel #2 | Vessel #3 |
| Day 0 | 12.66 | 11.74 | 13.91 | 12.46 | 12.46 | 11.96 |
| Day 3 | 97.88 | 95.98 | 93.25 | 76.08 | 78.64 | 71 |
| Day 4 | 181.07 | 188.45 | 183.55 | 123.67 | 107.26 | 110.23 |
| Day 5 | 255.44 | 261.47 | 255.72 | 125.92 | 118.7 | 122.02 |
| Day 6 | 304.31 | 313.6 | 297.6 | 126.48 | 119.46 | 117.2 |
| Day 7 | 293.8 | 305.07 | 296.57 | 100.41 | 101.57 | 109.41 |

TABLE 3-continued

Viable Cell Density (VCD) of C15 and C32 clonal cell
lines at different days of culture

| | Viable Cell Density ($10^5$ cells/ml) | | | | | |
|---|---|---|---|---|---|---|
| | C15 | | | C32 | | |
| | Vessel #1 | Vessel #2 | Vessel #3 | Vessel #1 | Vessel #2 | Vessel #3 |
| Day 10 | 329.38 | 326.06 | 326.28 | 119.43 | 109.95 | 97.38 |
| Day 11 | 314.02 | 313.79 | 299.71 | 103.32 | 88.29 | 80.48 |
| Day 12 | 290.26 | 313.71 | 293 | 94.73 | 86.48 | 73.51 |

Thus, based on the data as shown in Tables 2 and 3, clonal cell populations that have different growth characteristics despite being derived from the same parental cell line were identified.

Example 2: Analysis of Different Clonal Cell Populations by Copy Number Variation Analysis This example describes copy number variation analysis of the different clonal populations identified in Example 1 as having different growth characteristics.

In order to search for a possible basis for the difference in growth characteristics observed between the clonal cell lines as described in Examples 1a and 1b above, the different clonal cell lines were subject to copy number variation (CNV) analysis.

For the CNV analysis, whole genome re-sequencing (WGRS) data from 8 different cell lines were used: 4 clonal cell lines having high growth characteristics, including T3-9 25gen, T3-11 25gen, T3-6 100gen, and C15; 2 clonal cell lines having low growth characteristics: T3-6 25gen and C32; and 2 parental cell lines: Pfizer CHO1 and CHO2 (as described in Example 1). The WGRS data was mapped to CHO PICR genome (NCBI Accession GCF_003668045.1), using Burrows-Wheeler Aligner (BWA) software (available on GitHub). The read counts from 1kb bins were calculated using feature count tool from Subread software for all scaffolds. The number of reads for each sample were normalized to a total of 300 million reads, then used as input to the cn.mops software (Bioconductor) to make copy number calls. Circo plots were generated with circlize package circular visualization software.

This CNV analysis revealed that the cell lines having high growth characteristics had duplications of multiple regions of CHO chromosome 2. Details about the duplicated regions are provided below in Table 4. In total, the duplicated regions in chromosome 2 constituted 34.29 megabase (Mb). Since CHO chromosome 2 is 463.59 Mb in total length, the duplicated regions were calculated as constituting about 7.4% of CHO chromosome 2. For duplicated regions, two copies of the respective region of the chromosome were present (as compared to one copy of the respective region in the wild-type chromosome 2).

TABLE 4

Duplicated Regions of Chromosome 2 in Cells Having High Growth
Characteristics

| Scaffold | # Duplicated Nucleotides | Scaffold Length | % Scaffold Duplicated |
|---|---|---|---|
| NW_020822440.1 | 6292998 | 6576998 | 95.4 |
| NW_020822442.1 | 1868000 | 6068911 | 30.8 |

TABLE 4-continued

Duplicated Regions of Chromosome 2 in Cells Having High Growth
Characteristics

| Scaffold | # Duplicated Nucleotides | Scaffold Length | % Scaffold Duplicated |
|---|---|---|---|
| NW_020822459.1 | 15009966 | 15813966 | 94.9 |
| NW_020822466.1 | 11142077 | 11904077 | 93.6 |

This example shows that cell lines having high growth characteristics had duplications of multiple regions of CHO chromosome 2.

In an updated CHO genome assembly, PICRH (GenBank assembly accession: GCA_003668045.2), the contigs NW_020822440.1, NW_020822442.1, NW_020822459.1, NW_020822466.1 are included together in a larger contig NC_048595.1:160262188-196788751.

Example 3: Identification of Genes Duplicated in Cell Lines Having High Growth Characteristics This example describes the identification of genes that are duplicated in the region of CHO chromosome 2 identified in Example 2 as being present in clonal cell lines having high growth characteristics.

To identify genes in the region of CHO chromosome 2 identified in Example 2 as being duplicated in cell lines having high growth characteristics, differential gene analysis was performed by comparing the gene expression profiles of the cells having high growth characteristics and low growth characteristics, as described in Examples 1 and 2. For this analysis, paired-end RNA-Seq data were mapped to CHO PICR assembly (NCBI Accession Number: GCF_003668045.1) using subjunc program from Subread package (Sourceforge). Raw gene count was generated by featureCount from Subread package. To calculate the relative gene expression abundance across the transcriptome, FPKM (Fragments Per Kilobase Million) values were calculated with egdeR package (Bioconductor). Genes with FPKM value>1 were deemed as detectable above the technical noise. The differential expression statistics (log 2FC, AveExp, p-value, FDR) were computed by R Limma package (Bioconductor). The heatmap was generated with ComplexHeatmap package (Bioconductor).

In this analysis, 97 protein coding genes on the amplified regions of CHO chromosome 2 were identified as being significantly overexpressed (log FC>=0.7; FDR<=0.1). The 10 most significantly overexpressed genes (lowest False Discovery Rate (FDR)) are provided below in Table 5, with their NCBI gene ID (gene_id), chromosomal location (scaffold, start, end, strand), relative transcript abundance (Mean-DPKM) and DE statistics (log FC, adj.P.val, and MeanFPKM). As provided in Table 5, the 10 most significantly overexpressed genes are: Spire1, Nars, Rps14, Smim3, Fem1c, Ppic, Lmnb1, Me2, Pias2, and Sh3rf2. As shown further in Table 5, the genes Spire1, Nars, Rps14 and Smim3 are in scaffold region NW_020822466.1, the genes Fem1c, Ppic and Lmnb1 are in scaffold region NW_020822459.1, the genes Me2 and Pias2 are in scaffold region NW_020822440.1, and the gene Sh3rf2 is in scaffold region NW 020822442.1.

TABLE 5

| GeneID | Symbol | Scaffold | Start | End | Strand | LogFC | Adj. P Val. | Mean FPKM |
|---|---|---|---|---|---|---|---|---|
| | | 10 most overexpressed genes on CHO Chromosome 2 in cells having high growth characteristics | | | | | | |
| 100760597 | Spire1 | NW_020822466.1 | 4975799 | 5093233 | + | 1.09 | 1.68E−13 | 17.6 |
| 100764751 | Nars | NW_020822466.1 | 7906121 | 7922787 | + | 1.01 | 5.44E−12 | 56.3 |
| 100689292 | Rps14 | NW_020822466.1 | 11491494 | 11496142 | − | 1.11 | 5.6E−11 | 819.0 |
| 100763506 | Smim3 | NW_020822466.1 | 11747532 | 11790708 | + | 1.27 | 5.47E−10 | 7.6 |
| 100760897 | Fem1c | NW_020822459.1 | 2999236 | 3022635 | − | 1.01 | 3.45E−14 | 12.5 |
| 100774301 | Ppic | NW_020822459.1 | 9277844 | 9290654 | − | 1.07 | 4.18E−3 | 73.5 |
| 103161362 | Lmnb1 | NW_020822459.1 | 12327458 | 12367215 | + | 1.15 | 3.93E−2 | 56.2 |
| 100771311 | Me2 | NW_020822440.1 | 822108 | 867991 | − | 1.10 | 8.73E−11 | 18.6 |
| 100773121 | Pias2 | NW_020822440.1 | 3950610 | 4031509 | + | 1.01 | 1.06E−10 | 15.2 |
| 100762724 | Sh3r12 | NW_020822442.1 | 1209291 | 1314101 | − | 1.13 | 2.98E−11 | 10.0 |

Next, to further examine some of the genes identified above in the FPKM analysis as being overexpressed, the clonal cell lines T3-6 25 gen, T3-6 100 gen, and T3-9 25 gen were analyzed by quantitative PCR (qPCR) and quantitative reverse transcription PCR (qRT-PCR) to analyze gene copy number and mRNA abundance for genes of interest. Specifically, the cells were analyzed for Lmnb1, Seh1l, Sh3rf2, and Spire1 gene copy number, and for Pias2, Sh3rf2, Lmnb1, Rnmt, Seh1l, and Spire1 RNA quantity. (The genes Rnmt and Seh1l were also identified as being significantly overexpressed in the amplified region of CHO chromosome 2, but were not within the 10 most significantly overexpressed genes.)

FIG. 1A provides results of the gene copy number analysis. The X-axis lists the relevant gene (Lmnb1, Seh1l, Sh3rf2, and Spire1), and for each gene, three bars are shown. The bars depict the result for the respective gene from the following cell lines, in order from left to right: T3-6 25 gen, T3-6 100 gen, and T3-9 25 gen. The Y-axis provides the average copy number of the gene, per chromosome. As shown in FIG. 1A, for each of the Lmnb1, Seh1l, Sh3rf2, and Spire1 genes, there was an average copy of 1 copy of the gene per chromosome in the T3-6 25 gen cells. (Per Example 1, T3-6 25 gen cells have slow growth characteristics/relatively low VCD). In contrast, for each of these genes, there was an average copy of at least 1.5 copies of the gene per chromosome in the T3-6 100 gen, and T3-9 25 gen cells. (Per Example 1, T3-6 100 gen, and T3-9 25 gen cells have fast growth characteristics/relatively high VCD). These results show that that duplication of the CHO chromosome 2 genes Lmnb1, Seh1l, Sh3rf2, and Spire1 genes is associated with the change of cells from a slow-growing/low VCD phenotype to a fast-growing/high VCD phenotype.

Figure 1B:
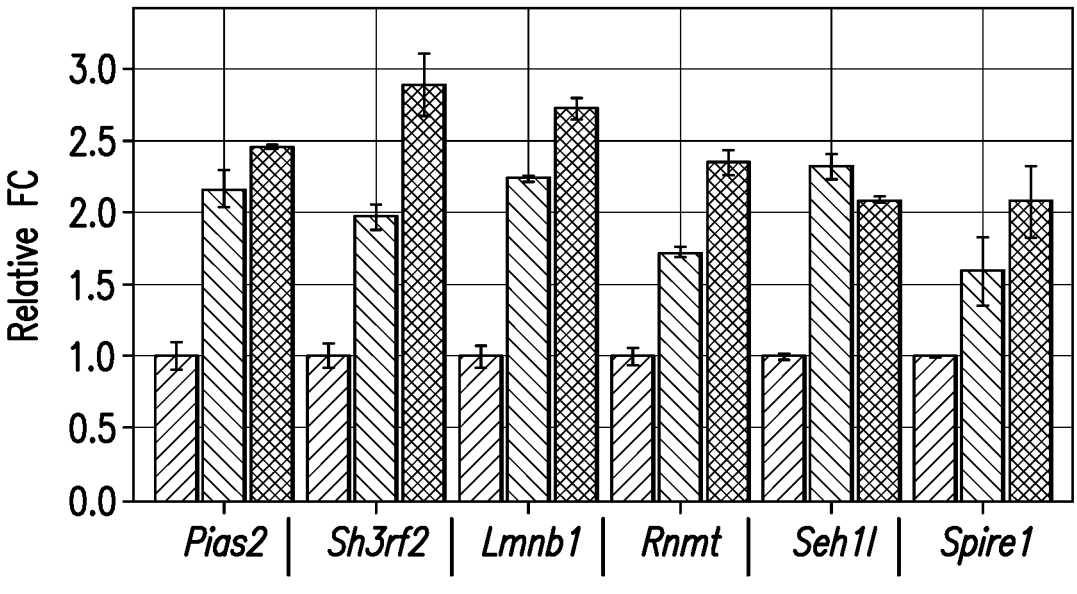
FIG. 1B depicts a bar graph showing mRNA abundance analysis for mRNA encoded by the genes Pias2, Sh3rf2, Lmnb1, Rnmt, Seh1l, and Spire1 in the clonal cell lines T3-6 25 gen, T3-6 100 gen, and T3-9 25 gen. The X axis lists the respective gene, and the Y axis lists the relative fold-change (FC) of the mRNA level (as compared to the mRNA level in the T3-6 25 gen cells). For each gene, three bars shown. In order from left to right, the three bars show the relative mRNA abundance for mRNA encoded by the respective gene per chromosome 2 in T3-6 25 gen, T3-6 100 gen.

FIG. 1B provides results of the mRNA abundance analysis. The X-axis lists the relevant gene (Pias2, Sh3rf2, Lmnb1, Rnmt, Seh1l, Spire1), and for each gene, three bars are shown. The bars depict the result for the respective gene from the following cell lines, in order from left to right: T3-6 25 gen, T3-6 100 gen, and T3-9 25 gen. The Y-axis provides the relative fold-change (FC) of the mRNA level for each respective gene (the T3-6 25 gen value was assigned "1"; the T3-6 100 gen and T3-9 25 gen values are relative to the T3-6 25 gen value). As shown in FIG. 1B, for each of Pias2, Sh3rf2, Lmnb1, Rnmt, Seh1l, and Spire1, the mRNA relative FC value for the T3-6 100 gen cells and T3-9 25 gen cells was at least 1.5 or 2 times the value, respectively, as for T3-6 25 gen cells. (Per Example 1, T3-6 100 gen, and T3-9 25 gen cells have fast growth characteristics/relatively high VCD, and T3-6 25 gen cells have slow growth characteristics/relatively low VCD.) These results show that increased mRNA levels of the genes Pias2, Sh3rf2, Lmnb1, Rnmt, Seh1l, and Spire1 associated with the change of cells from having low growth characteristics to high growth characteristics.

Overall, this example shows that duplication of the CHO chromosome 2 genes Spire1, Nars, Rps14, Smim3, Fem1c, Ppic, Lmnb1, Me2, Pias2, Sh3rf2, Rnmt, and Seh1 is associated with increased growth of CHO cells.

It is claimed:

1. A Chinese Hamster Ovary (CHO) mammalian host cell comprising an exogenous nucleic acid and a duplication of at least one gene selected from the group consisting of: Spire1, Nars, Rps14, Smim3, Fem1c, Ppic, Lmnb1, Me2, Pias2, Sh3rf2, Rnmt, and Sehl1, wherein the Spirel gene encodes a polypeptide comprising the amino acid sequence of SEQ ID NO: 1; wherein the Nars gene encodes a polypeptide comprising the amino acid sequence of SEQ ID NO: 2; wherein the Rps14 gene encodes a polypeptide comprising the amino acid sequence of SEQ ID NO: 3; wherein the Smim3 gene encodes a polypeptide comprising the amino acid sequence of SEQ ID NO: 4; wherein the Fem 1c gene encodes a polypeptide comprising the amino acid sequence of SEQ ID NO: 5; wherein the Ppic gene encodes a polypeptide comprising the amino acid sequence of SEQ ID NO: 6; wherein the Lmnb 1 gene encodes a polypeptide comprising the amino acid sequence of SEQ ID NO: 7; wherein the Me2 gene encodes a polypeptide comprising the amino acid sequence of SEQ ID NO: 8; wherein the Pias2 gene encodes a polypeptide comprising the amino acid sequence of SEQ ID NO: 9; wherein the Sh3rf2 gene encodes a polypeptide comprising the amino acid sequence of SEQ ID NO: 10; and wherein the host cell has an improved growth characteristic as compared to an otherwise identical host cell lacking duplication of the at least one gene.

2. The CHO host cell of claim 1, comprising a duplication of at least two genes, wherein one of the at least two gens is selected from the group consisting of: Spire1, Nars, Rps14, and Smim3, and one of the at least two genes is selected from the group consisting of: Fem1c, Ppic, Lmnb1, Me2, Pias2, and Sh3rf2.

3. The CHO host cell of claim 1, comprising a duplication of at least four genes:

wherein one of the at least four genes is selected from the group consisting of: Spire1, Nars, Rps14, and Smim3;

wherein one of the at least four genes is selected from the group consisting of: Fem1c, Ppic, and Lmnb1;

wherein one of the at least four genes is selected from the group consisting of: Me2 and Pias2; and wherein one of the at least four genes is Sh3rf2.

4. A method of selecting a Chinese Hamster Ovary (CHO) host cell having an improved growth characteristic, the method comprising:

(a) assaying a CHO host cell comprising an exogenous nucleic acid for duplication of at least one gene selected from the group consisting of: Spire1, Nars, Rps14, Smim3, Fem1c, Ppic, Lmnb1, Me2, Pias2, Sh3rf2, Rnmt, and Sehl1, wherein the Spirel gene encodes a polypeptide comprising the amino acid sequence of SEQ ID NO: 1; wherein the Nars gene encodes a polypeptide comprising the amino acid sequence of SEQ ID NO: 2; wherein the Rps14 gene encodes a polypeptide comprising the amino acid sequence of SEQ ID NO: 3; wherein the Smim3 gene encodes a polypeptide comprising the amino acid sequence of SEQ ID NO: 4; wherein the Fem 1c gene encodes a polypeptide comprising the amino acid sequence of SEQ ID NO: 5; wherein the Ppic gene encodes a polypeptide comprising the amino acid sequence of SEQ ID NO: 6; wherein the Lmnb 1 gene encodes a polypeptide comprising the amino acid sequence of SEQ ID NO: 7; wherein the Me2 gene encodes a polypeptide comprising the amino acid sequence of SEQ ID NO: 8; wherein the Pias2 gene encodes a polypeptide comprising the amino acid sequence of SEQ ID NO: 9; wherein the Sh3rf2 gene encodes a polypeptide comprising the amino acid sequence of SEQ ID NO: 10; and (b) selecting the CHO host cell comprising duplication of the at least one gene, wherein the assaying step (a) comprises fluorescent in situ hybridization (FISH), comparative genomic hybridization, microarray based systems, whole genome sequencing or a combination thereof, and wherein the CHO host cell comprising duplication of the at least one gene has an improved growth characteristic as compared to an otherwise identical CHO host cell lacking duplication of the at least one gene.

5. The method of claim 4, wherein the CHO host cell is assayed for duplication of at least two genes and wherein one of the at least two genes is selected from the group consisting of: Spire1, Nars, Rps14, Smim3, and one of the at least two genes is selected from the group consisting of: Fem1c, Ppic, Lmnb1, Me2, Pias2, and Sh3rf2.

6. A method for producing a recombinant protein, the method comprising:
(a) providing the CHO host cell of claim 1, wherein the exogenous nucleic acid of the host cell encodes a recombinant protein;
(b) culturing the CHO host cell under conditions sufficient to express the recombinant protein.

7. A method for producing a recombinant protein, the method comprising:
(a) providing a CHO host cell selected according to the method of claim 4, wherein the exogenous nucleic acid of the host cell encodes a recombinant protein;
(b) culturing the CHO host cell under conditions sufficient to express the recombinant protein.

8. The method of claim 6, further comprising recovering the expressed recombinant protein.

9. The CHO host cell of claim 1, wherein the exogenous nucleic acid encodes a protein.

10. The CHO host cell of claim 9, wherein the protein is an antibody or a cytokine.

11. A method of preparing a Chinese Hamster Ovary (CHO) host cell having an improved growth characteristic, the method comprising:
introducing an exogenous nucleic acid molecule comprising the sequence of at least one gene selected from the group consisting of: Spire1, Nars, Rps14, Smim3, Fem1c, Ppic, Lmnb1, Me2, Pias2, Sh3rf2, Rnmt, and Sehll1 into the CHO host cell,
wherein the Spire1 gene encodes a polypeptide comprising the amino acid sequence of SEQ ID NO: 1; wherein the Nars gene encodes a polypeptide comprising the amino acid sequence of SEQ ID NO: 2; wherein the Rps14 gene encodes a polypeptide comprising the amino acid sequence of SEQ ID NO: 3; wherein the Smim3 gene encodes a polypeptide comprising the amino acid sequence of SEQ ID NO: 4; wherein the Fem 1c gene encodes a polypeptide comprising the amino acid sequence of SEQ ID NO: 5; wherein the Ppic gene encodes a polypeptide comprising the amino acid sequence of SEQ ID NO: 6; wherein the Lmnb 1 gene encodes a polypeptide comprising the amino acid sequence of SEQ ID NO: 7; wherein the Me2 gene encodes a polypeptide comprising the amino acid sequence of SEQ ID NO: 8; wherein the Pias2 gene encodes a polypeptide comprising the amino acid sequence of SEQ ID NO: 9; wherein the Sh3rf2 gene encodes a polypeptide comprising the amino acid sequence of SEQ ID NO: 10; and wherein the host cell comprising the exogenous nucleic acid molecule has an improved growth characteristic as compared to an otherwise identical CHO host cell that does not contain the exogenous nucleic acid molecule.

12. The method of claim 11, wherein one or more exogenous nucleic acid molecules comprising the sequence of at least two of the at least one genes are introduced into the host cell.

13. The method of claim 12, wherein one of the at least two genes is selected from the group consisting of: Spire1, Nars, Rps14, Smim3, and one of the at least two genes is selected from the group consisting of: Fem1c, Ppic, Lmnb1, Me2, Pias2, and Sh3rf2.

14. The CHO host cell of claim 1, wherein the exogenous nucleic acid is chromosomally-integrated in a host cell chromosome.

15. The CHO host cell of claim 1, wherein the improved growth characteristic is greater cell count, greater viable cell count, greater cell density, or greater viable cell density of a first cell culture comprising the cell having an improved growth characteristic as compared to a second cell culture comprising the otherwise identical CHO host cell lacking duplication of the gene(s), wherein the first and second cell cultures are grown under the same conditions and for the same time period.

16. The method of claim 7, further comprising recovering the recombinant protein.

17. The method of claim 7, wherein the exogenous nucleic acid encodes a protein and wherein the protein is an antibody or a cytokine.

\* \* \* \* \*